(12) United States Patent
Park et al.

(10) Patent No.: US 11,209,512 B2
(45) Date of Patent: Dec. 28, 2021

(54) METHOD FOR ACQUIRING VARIABLE SLAB MAGNETIC RESONANCE IMAGING DATA

(71) Applicant: KOREA ADVANCED INSTITUTE OF SCIENCE AND TECHNOLOGY, Daejeon (KR)

(72) Inventors: Sung-Hong Park, Daejeon (KR); Won-Joon Do, Daejeon (KR)

(73) Assignee: KOREA ADVANCED INSTITUTE OF SCIENCE AND TECHNOLOGY

( * ) Notice: Subject to any disclaimer, the term of this patent is extended or adjusted under 35 U.S.C. 154(b) by 159 days.

(21) Appl. No.: 16/496,097

(22) PCT Filed: Oct. 16, 2017

(86) PCT No.: PCT/KR2017/011375
§ 371 (c)(1),
(2) Date: Sep. 20, 2019

(87) PCT Pub. No.: WO2018/174360
PCT Pub. Date: Sep. 27, 2018

(65) Prior Publication Data
US 2020/0096585 A1    Mar. 26, 2020

(30) Foreign Application Priority Data
Mar. 21, 2017    (KR) .................. 10-2017-0035099

(51) Int. Cl.
*G01R 33/54* (2006.01)
*G01R 33/44* (2006.01)
(Continued)

(52) U.S. Cl.
CPC ............ *G01R 33/543* (2013.01); *A61B 5/055* (2013.01); *G01R 33/446* (2013.01); *G01R 33/4822* (2013.01); *G01R 33/5635* (2013.01)

(58) Field of Classification Search
CPC ............. G01R 33/543; G01R 33/4822; G01R 33/446; G01R 33/5635; G01R 33/565;
(Continued)

(56) References Cited

U.S. PATENT DOCUMENTS

2009/0278538 A1    11/2009    Chen
2011/0213237 A1     9/2011    Park
(Continued)

OTHER PUBLICATIONS

Do, Won-Joon, et al. "Artifact-suppressed optimal three-dimensional T1-and T2*-weighted dual-echo imaging." Magnetic resonance in medicine 76.5 (2015): 1504-1511. (Year: 2015).*
(Continued)

*Primary Examiner* — Rishi R Patel
(74) *Attorney, Agent, or Firm* — Stuart H. Mayer; Mayer & Williams PC

(57) ABSTRACT

The present invention relates to a method for acquiring data for acquiring an arteriogram and a venogram of magnetic resonance imaging, the method: using one or more echo; and simultaneously acquiring, through one-time photography, an arteriogram and a venogram, which are optimized according to the number of slabs or improving connectivity of a slab boundary part of the arteriogram.

16 Claims, 19 Drawing Sheets

(51) Int. Cl.
    *G01R 33/563*     (2006.01)
    *G01R 33/48*     (2006.01)
    *A61B 5/055*     (2006.01)

(58) Field of Classification Search
    CPC .......... G01R 33/4818; G01R 33/56536; A61B 5/055
    See application file for complete search history.

(56) References Cited

U.S. PATENT DOCUMENTS

| | | |
|---|---|---|
| 2011/0275926 A1 | 11/2011 | Du |
| 2013/0225976 A1 | 8/2013 | Miyazaki et al. |
| 2014/0081123 A1 | 3/2014 | Korosec et al. |
| 2016/0116560 A1* | 4/2016 | Chen ...................... A61B 5/055 324/309 |
| 2018/0024216 A1* | 1/2018 | Gilbert .................. A61B 5/489 324/309 |

OTHER PUBLICATIONS

Park, Sung-Hong, Chan-Hong Moon, and Kyongtae Ty Bae. "Compatible dual-echo arteriovenography (CODEA) using an echo-specific K-space reordering scheme." Magnetic Resonance in Medicine: An Official Journal of the International Society for Magnetic Resonance in Medicine 61.4 (2009): 767-774. (Year: 2009).*

* cited by examiner (a)

(b)

METHOD FOR ACQUIRING VARIABLE SLAB MAGNETIC RESONANCE IMAGING DATA

TECHNICAL FIELD

The present invention relates to a data acquisition method for a magnetic resonance image, which uses one or more echoes and relates to a technique for acquiring arteriograms and venograms at once or improving the quality of arteriograms by one shot.

BACKGROUND ART

Magnetic resonance image is an imaging technique that uses the principle of nuclear magnetic resonance. When the human body is put into a magnetic resonance imaging apparatus that generates a magnetic field and generates a high frequency, electrons of hydrogen atoms in the body resonate. When measuring a difference in signals outputted at this time and reconstructing and imaging them through a computer, magnetic resonance image is generated.

In order to acquire a magnetic resonance image, Time-of-flight MR angiography and/or blood oxygenation level dependent MR venogram may be used.

On the other hand, compatible dual-echo arteriovenography (CODEA) technique is a technology that can acquire the image of the time-of-flight MR angiography and the blood oxygenation level dependent MR venogram at the same time.

Generally, in relation to time-of-flight MR angiography, blood vessels are better detected when shooting with multiple slabs and in relation to Blood oxygenation level dependent MR venogram, shooting with one slab improves SNR.

The existing COEA technique allows acquiring arteriogram and venogram at the same time, but there is a problem in optimizing the number of slabs. Also, in a case of using conventional time-of-flight MR angiography, when shooting with multiple slabs, artifacts may occur at the slab boundary.

DISCLOSURE OF THE INVENTION

Technical Problem

In order to solve the above problems, the present invention is to provide a data acquisition method and an image processing method for simultaneously acquiring the arteriogram and venogram optimized according to the number of slabs in one shot or improving the connectivity of the slab boundary portion of the arteriogram.

Technical Solution

An aspect of the present invention can provide an image acquisition method (=data acquisition method) using one or more echo. At this time, the data acquisition method includes a first process of exciting a plurality of times the first RF 110 to excite only the first slab 11 of the plurality of slabs 11 and 12, and each time the first RF 110 is excited, the first echo 111 acquires the low frequency component 211 according to a predetermined order, and the second echo 112 acquires the high frequency component 221 according to the predetermined order. After the first process, the method includes a second process to excite the second RF 120 to excite only the second slab 12 of the plurality of slabs a plurality of times, and each time the second RF 120 is excited, the first echo 121 acquires the low frequency component 212 in a predetermined order, and the second echo 122 acquires the high frequency component 222 according to the predetermined order. After the second process, the method includes a third process of exciting the third RF 130 multiple times to excite the entire slab (=entire slab) 10 at once, and each time the third RF 130 is excited, the first echo 131 acquires a high frequency component 213 in a predetermined order, and the second echo 132 acquires a low frequency component 223 in a predetermined order.

At this time, the method may include generating a first low frequency sub-image 511 by transforming first low frequency phase encoding lines 211 acquired from the first echoes of the first process into an image region; generating second low frequency sub-images 512 by transforming second low frequency phase encoding lines 212 acquired from the first echoes of the second process into an image region; combining the first low frequency sub-image 511 and the second low frequency sub-image 512 to generate a third low frequency sub-image 611; transforming the third low frequency sub-image 611 into a frequency domain to acquire a first low frequency data set 311; acquiring the first K-space data 210 by combining the first low frequency data set 311 and third high frequency phase encoding lines 312 acquired from the first echoes of the third process in a frequency domain.

At this time, the method may include generating first high frequency sub-images 721 by transforming first high frequency phase encoding lines 221 acquired from the second echoes of the first process into an image region; generating second high frequency sub-images 722 by transforming second high frequency phase encoding lines 222 acquired from the second echoes of the second process into an image region; and combining the first high frequency sub-image 721 and the second high frequency sub-image 722 to generate a third high frequency sub-image 421, transforming the third high frequency sub-image 421 into a frequency domain to acquire a second high frequency data set 321; and acquiring second K-space data 220 by combining the second high frequency data set and the third low frequency phase encoding lines 322 acquired from the second echoes of the third process in a frequency domain.

Alternatively, first low frequency phase encoding lines 211 acquired from the first echoes of the first process, second low frequency phase encoding lines 212 acquired from the first echoes of the second process, and the third high frequency phase encoding lines 213 acquired from the first echoes of the third process are transformed into image regions, respectively, thereby combining them with each other in the image region.

Then, first high frequency phase encoding lines 221 acquired from the second echoes of the first process, second high frequency phase encoding lines 222 acquired from the second echoes of the second process, and the third low frequency phase encoding lines 223 acquired from the second echoes of the third process are transformed into image regions, respectively, thereby combining them with each other in the image region.

In this case, the shooting conditions in the first echo and the shooting conditions in the second echo may be different.

In this case, the first echo precedes the second echo and a Time of Flight MR angiogram may be acquired at the time of the first echo, and susceptibility weighted imaging may be acquired at the time of the second echo.

In this case, the number of slabs at the time of the first echo may be greater than the number of slabs at the time of the second echo.

In this case, an arterial image may be acquired at the time of the first echo, and a venous image may be acquired at the time of the second echo.

Another aspect of the present invention can provide a data acquisition method using one or more echoes. At this time, the data acquisition method may be characterized in acquiring low frequency lines 211 and high frequency lines 221 of the K-space lines with respect to each of the first echo 111 and the second echo 112 generated by exciting the first RF signal 110 with respect to the first slab 11, acquiring low frequency lines 212 and high frequency lines 222 of the K-space lines with respect to each of the third echo 121 and the fourth echo 122 generated by exciting the second RF signal 120 with respect to the second slab 12, acquiring high frequency lines 213 in the fifth echo 131 generated by exciting the third RF signal 130 with respect to the entire slab 10 including the first slab 11 and the second slab 12, and acquiring low frequency lines 223 in the sixth echo 132.

Here, the first echo 111 may be the first echo for the first RF signal 110, and the second echo 112 may be the second echo for the first RF signal 110.

Then, the third echo 121 may be a first echo for the second RF signal 120, and the fourth echo 122 may be a second echo for the second RF signal 120.

Then, the fifth echo 131 may be a first echo for the third RF signal 130, and the sixth echo 132 may be a second echo for the third RF signal 130.

In this case, the first echo may precede the second echo, or the second echo may precede the first echo.

Another aspect of the present invention can provide a data acquisition method using one or more echoes. The data acquisition method may acquire some lines 211 and 212 according to the first ordering in the first echoes 111 and 121 for the first slab 11 and the second slab 12, respectively, acquire some lines 221 and 222 according to the second ordering in the second echo 112 and 122, acquire at least a portion 213 of the remaining lines according to the first ordering in the first echo 131 for the entire slab 10, and acquire at least some of the remaining lines 223 according to the second order in the second echo 132.

A data acquisition method according to another aspect of the present invention may include acquiring some lines 211 and 212 according to the first ordering for each of the first slab 11 and the second slab 12, acquiring residual lines 213 according to the first ordering for the entire slab 10, and combining information on the some lines and the remaining lines with each other.

Another aspect of the present invention can provide a data acquisition method using one or more echoes. The data acquisition method acquires the low frequency lines 211 and 212 in the first echoes 111 and 121 with respect to the plurality of slabs 11 and 12 defined by dividing the entire slab 10, acquires the high frequency lines 221 and 222 in the second echo 112 and 122, acquires a high frequency line 213 in the first echo 131 for the entire slab 10, and acquires the low frequency line 223 in the second echo 132.

According to another aspect of the present invention, it is possible to provide a data acquisition method using one or more echoes. At this time, the data acquisition method includes performing, by an MRI device, a first process that includes acquiring a low frequency component of a first echo generated by exciting a first RF signal with respect to a first slab; performing, by the MRI device, a second process that includes acquiring a low frequency component of a third echo generated by exciting a second RF signal with respect to a second slab; and performing, by the MRI device, a third process that includes acquiring a high frequency component of a fifth echo generated by exciting a third RF signal with respect to an entire slab including the first slab and the second slab.

At this time, the first process may further include acquiring a high frequency component with respect to a second echo generated by exciting the first RF signal with respect to the first slab, the second process may further include acquiring a high frequency component with respect to a fourth echo generated by exciting the second RF signal with respect to the second slab, and the third process may further include acquiring a low frequency component in a sixth echo generated by exciting the third RF signal with respect to the entire slab including the first slab and the second slab.

In this case, the first echo may be an echo generated earlier than the second echo, the third echo may be an echo generated earlier than the fourth echo, and the fifth echo may be an echo generated earlier than the sixth echo.

In this case, the first echo may be the first echo generated by exciting the first RF signal, the second echo may be the second echo generated by exciting the first RF signal, the third echo may be the first echo generated by exciting the second RF signal, the fourth echo may be the second echo generated by exciting the second RF signal, the fifth echo may be the first echo generated by exciting the third RF signal, and the sixth echo may be the second echo generated by exciting the third RF signal.

In addition, the data acquisition method, the first process may be configured to excite the first RF a plurality of times, and each time the first RF is excited, the first echo may be configured to acquire low frequency lines among K-space lines in a predetermined order, and the second process may be configured to excite the second RF a plurality of times, and each time the second RF is excited, the third echo may be configured to acquire low frequency lines among K-space lines in a predetermined order, and the third process may be configured to excite the third RF a plurality of times, and each time the third RF is excited, the fifth echo may be configured to acquire high frequency lines among K-space lines in a predetermined order.

In addition, the first process may be configured to excite the first RF a plurality of times, and each time the first RF is excited, the first echo may acquire low frequency lines among K-space lines in a predetermined order, and in the second echo, high-frequency lines among K-space lines may be acquired in a predetermined order, the second process may be configured to excite the second RF a plurality of times, and each time the second RF is excited, the third echo may acquire low frequency lines among K-space lines in a predetermined order, and in the fourth echo, high-frequency lines among the K-space lines may be acquired in a predetermined order, and the third process may be configured to excite the third RF a plurality of times, and each time the third RF is excited, the fifth echo may acquire high frequency lines among K-space lines in a predetermined order, and in the sixth echo, low-frequency lines among K-space lines may be acquired in a predetermined order.

At this time, the data acquisition method may include generating, by a computing device, a first low frequency sub-image by transforming first low frequency phase encoding lines acquired in the first echo of the first process into an image region; generating, by the computing device, a second low frequency sub-image by transforming second low frequency phase encoding lines acquired in the third echo of the second process into an image region; generating, by the computing device, a third low frequency sub-image by combining the first low frequency sub-image and the second low frequency sub-image; transforming, by the computing device, the third low frequency sub-image into a frequency domain to acquire a first low frequency data set; and acquiring, by the computing device, first K-space data by combining the first low frequency data set and the third high frequency phase encoding lines acquired in the fifth echo of the third process in a frequency domain.

In addition, the data acquisition method may further include generating, by a computing device, a first high frequency sub-image by transforming first high frequency phase encoding lines acquired in the second echo of the first process into an image region; generating, by the computing device, a second high frequency sub-image by transforming second high frequency phase encoding lines acquired in the fourth echo of the second process into an image region; generating, by the computing device, a third high frequency sub-image by combining the first high frequency sub-image and the second high frequency sub-image; transforming, by the computing device, the third high frequency sub-image into a frequency domain to acquire a second high frequency data set; and acquiring, by the computing device, second K-space data by combining the second high frequency data set and the third low frequency phase encoding lines acquired in the sixth echo of the third process with each other in a frequency domain.

In addition, the data acquisition method may include transforming, by a computing device, first low frequency phase encoding lines acquired in the first echo of the first process, second low frequency phase encoding lines acquired in the third echo of the second process, and third high frequency phase encoding lines acquired in the fifth echo of the third process into an image region to combine them each other in an image region, and transforming, by a computing device, first high frequency phase encoding lines acquired in the second echo of the first process, second high frequency phase encoding lines acquired in the fourth echo of the second process, and third low frequency phase encoding lines acquired in the sixth echo of the third process into an image region to combine them each other in an image region.

In this case, the shooting conditions in the first echo and the shooting conditions in the second echo may be different.

In this case, a Time of Flight MR angiogram may be acquired at the time of the first echo, and susceptibility weighted imaging may be acquired at the time of the second echo.

In this case, the arterial image is acquired by using the data acquired in the first echo, the third echo, and the fifth echo, and the venous image may be acquired by using data acquired in the second echo, the fourth echo, and the sixth echo.

In addition, the data acquisition method may include acquiring some lines according to a first ordering in the first echo with respect to the first slab, acquiring some lines according to a second ordering in the second echo, acquiring some lines according to a third ordering in the third echo with respect to the second slab, acquiring some lines according to a fifth ordering in the fourth echo, acquiring at least some of the remaining lines according to a fifth ordering in the fifth echo with respect to the entire slab, and acquiring at least some of the remaining lines according to a sixth ordering in a sixth echo.

A data acquisition method according to another aspect of the present invention may include acquiring, by the MRI device, some lines according to a first ordering with respect to each of a first slab and a second slab; acquiring, by the MRI device, remaining lines according to the first ordering with respect to an entire slab; and combining, by the MRI device, information on the some lines and the remaining lines with each other.

Another aspect of the present invention provides a computer-readable non-transitory storage medium in which instruction codes for operating an MRI device are recorded, may be provided. At this time, the instruction code allows the MRI device to perform a first process including acquiring a low frequency component of a first echo generated by exciting the first RF signal with respect to a first slab, allows the MRI device to perform a second process including acquiring a low frequency component of a third echo generated by exciting a second RF signal with respect to a second slab, and allows the MRI device to perform a third process including acquiring a high frequency component of a fifth echo generated by exciting a third RF signal with respect to the entire slab including the first slab and the second slab.

Advantageous Effects

According to the present invention, the arteriogram and the venogram optimized according to the number of slabs can be simultaneously acquired in one shot or the slab boundary connectivity of the arteriogram can be improved.

MODE FOR CARRYING OUT THE INVENTION

Hereinafter, embodiments of the present invention will be described with reference to the accompanying drawings. However, the present invention is not limited to the embodiments described herein, but may be implemented in various other forms. The terminology used herein is for the purpose of understanding the embodiments and is not intended to limit the scope of the present invention. In addition, the singular forms used below include plural forms unless the phrases expressly have the opposite meaning.

First Embodiment—Acquisition of K-Space Data

Figure 1:
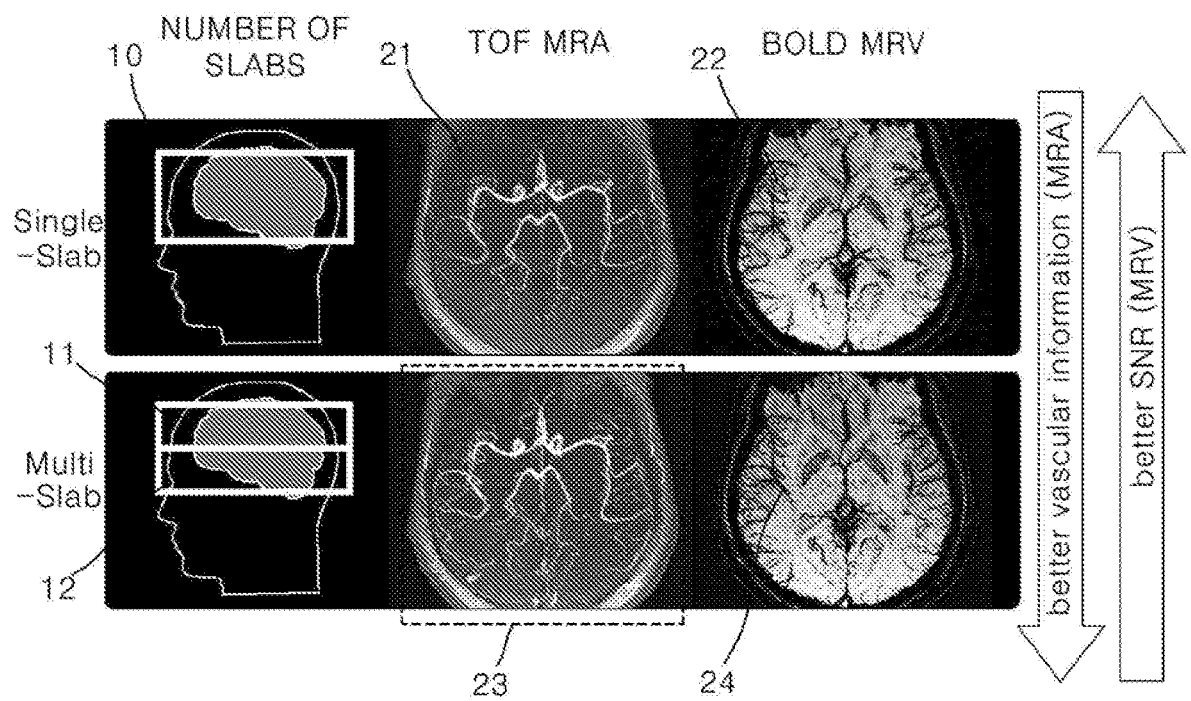
FIG. 1 is a view for explaining the quality of an image according to the number of slabs according to the first embodiment of the present invention.

FIG. 1 is a view for explaining the quality of an image according to the number of slabs according to the first embodiment of the present invention.

When shooting with an entire slab (i.e., one slab) 10, blood vessels may not well detected in an image 21 of Time-of-flight MR angiography (TOF MRA), but SNR may be improved in an image 22 of Blood oxygenation level dependent MR venogram (BOLD MRV).

On the other hand, when shooting by dividing the entire slab 10 into several slabs 11 and 12, blood vessels are better detected in the image 23 of TOF MRA, but the SNR in the image 24 of BOLD MRV is worse than when shooting with the entire slab 10.

Conventional compatible dual-echo arteriovenography (CODEA) is a technique that allows simultaneous acquisition of TOF MRA and BOLD MRV, but does not optimize the number of slabs.

In the first embodiment, arteriogram and venogram, which are differently optimized according to the number of slabs, may be simultaneously acquired in one shot.

In order to acquire a set of TOF MRA images 21 and BOLD MRV) images 22, the MRI data acquisition target 10 is divided into N (e.g., N=2) slabs (e.g., 11 and 12) and processed. That is, when the MRI data acquisition target 10 is named 'entire slab', the entire slab 10 may include a first slab 11 and a second slab 12 that do not overlap each other.

Figure 2:
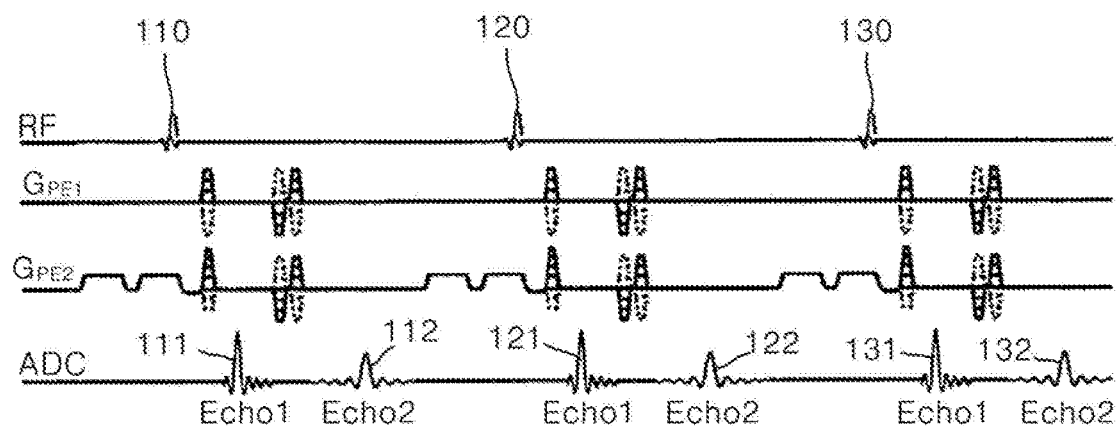
FIG. 2 illustrates an RF pulse waveform and an echo waveform over time according to a first embodiment of the present invention.

FIG. 2 illustrates an RF pulse waveform, a waveform for a method of acquiring a phase encoding line, and an echo waveform over time according to the first embodiment of the present invention.

In general, when a slab is divided into a plurality of slabs, a plurality of RF pulses may be generated for each slab. In FIG. 2 of the present invention, for convenience of description, it is shown that one RF pulse of a plurality of RF pulses is generated for each slab.

In the K-space data acquisition method according to the first embodiment of the present invention, when the number of slabs to be divided is N (e.g., N=2), the RF pulse may be generated N+1 times or more. That is, the first RF pulse excitation 110, the second RF pulse excitation 120, and the third RF pulse excitation 130 may be sequentially performed.

In this case, conventionally, one echo (e.g., 111) may be generated for each RF pulse excitation (e.g., 110). Generally, multiple RF pulse excitations can be generated to acquire sophisticated images. However, there is a problem in that it takes a long time in such a case.

Accordingly, in one embodiment of the present invention, two echoes (e.g., 111 and 112) may be generated for each RF pulse excitation (e.g., 110).

In this case, the waveforms of two echoes for each RF pulse excitation may be determined according to waveforms (e.g., waveforms of G PE1 and G PE2) for a method for acquiring a phase encoding line. For example, the waveform of the first echo 111 may be determined according to the first scheme 51, and the waveform of the second echo 112 may be determined according to the second scheme 52. At this time, the intensity of the signal decreases as time passes from the time point when the RF pulse excitation occurs. Therefore, in order to acquire a lot of data in the second echo 112, the scheme for acquiring the phase encoding line may be identical to the centric PE order scheme.

Also, in another embodiment of the present invention, only one echo (e.g., 111) may be generated for each RF pulse excitation (e.g., 110).

Figure 3:
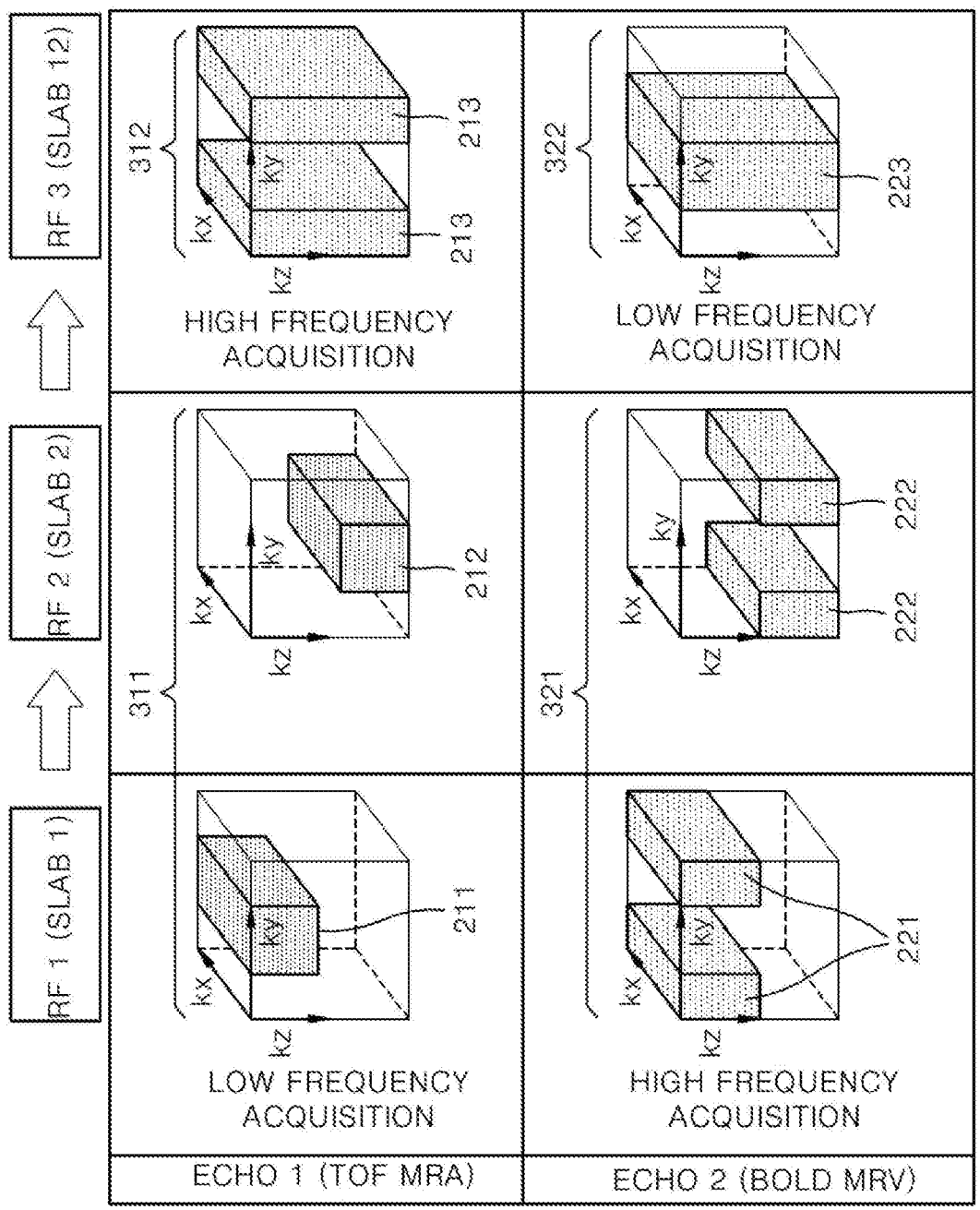
FIG. 3 is a schematic diagram of data acquisition in K-space according to the first embodiment of the present invention.

FIG. 3 is a schematic diagram of data acquisition in K-space according to the first embodiment of the present invention.

In this case, the K-space may mean a 3D space, the x-axis of each K-space may mean time, the y-axis may mean frequency, and the z-axis may mean the height of the slab (e.g., 11).

Figure 4:
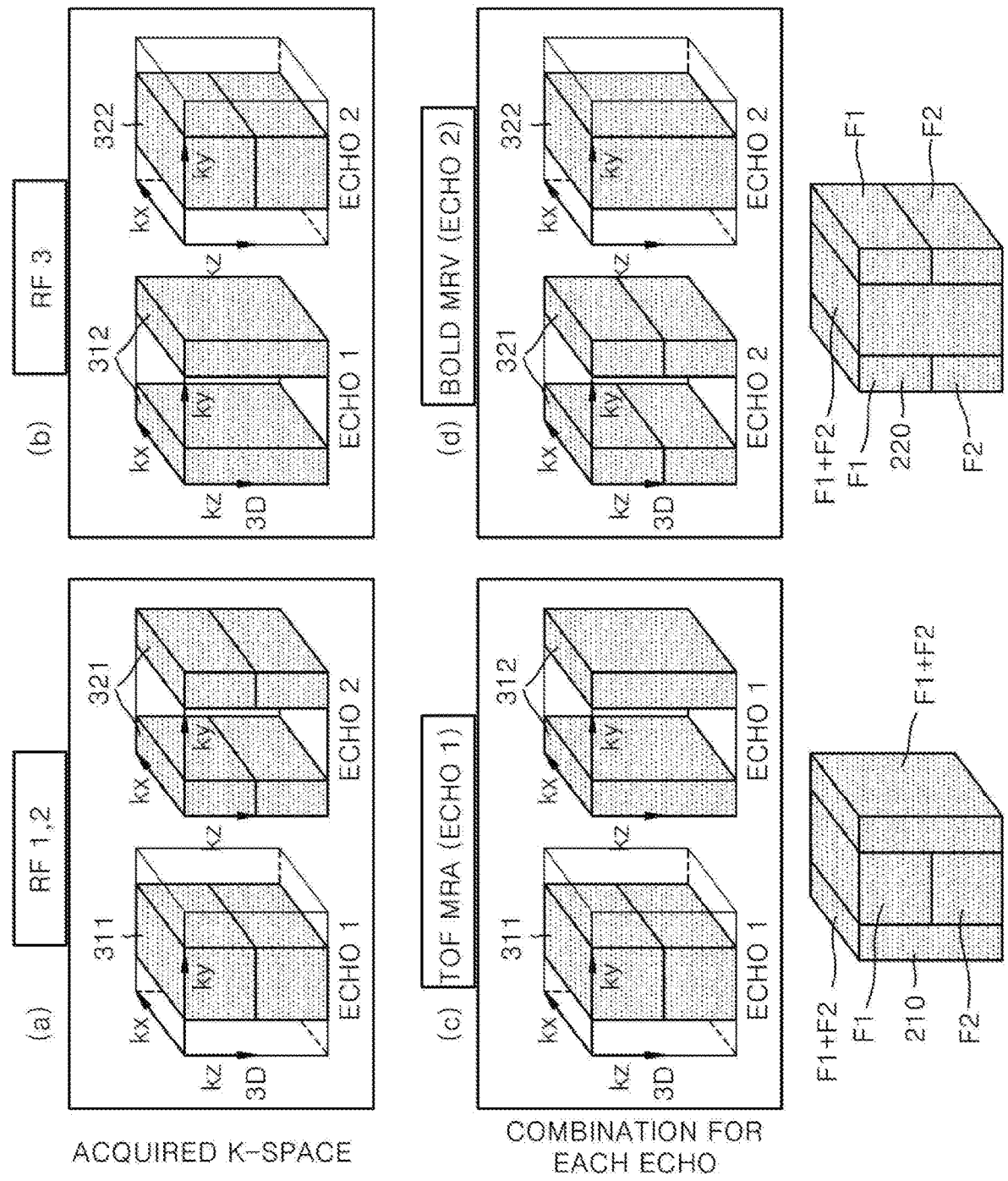
FIG. 4 shows a data structure in K-space according to the first embodiment of the present invention.

FIG. 4 shows a data structure in K-space according to the first embodiment of the present invention. FIG. 4(*a*) shows the acquired K-space for the first RF and the second RF, FIG. 4(*b*) shows the acquired K-space for the third RF, FIG. 4(*c*) shows the combination of each echo for TOF MRA, and FIG. 4(*d*) shows the combination for each echo for BOLD MRV.

FIGS. 3 and 4 illustrate a case where two echoes (first echo and second echo) are generated for each RF pulse excitation.

However, unlike this, in another embodiment of the present invention, only one echo (first echo) can be generated for each RF pulse excitation, and in this case, the contents related to the second echo among the contents shown in FIGS. 3 and 4 may be removed and presented.

Hereinafter, this will be described with reference to FIGS. 1 and 4.

The K-space data acquisition method according to the first embodiment of the present invention may include the following operations.

Operation (S110):

For each of the first RF pulse excitation 110 to the second RE pulse excitation 120, K-space data for the first slab 11 to the second slab 12 may be acquired.

In this case, for each of the first RF pulse excitation 110 to the second RF pulse excitation 120, a phase encoding line corresponding to a different frequency domain in a plurality of echoes ([111, 112] or [121, 122]) can be acquired.

That is, for each of the first RF pulse excitation 110 to the second RF pulse excitation 120, the first low frequency phase encoding lines 211 to the second low frequency phase encoding lines 212 may be acquired with respect to the first echo 111 or 121 among the plurality of echoes, and first high frequency phase encoding lines 221 to second high frequency phase encoding lines 222 may be acquired with respect to the second echo 112 or 122. In this case, preferably, the first echo 111 or 121 may be an echo that precedes the second echo 112 or 122 on the time axis.

Here, for each of the first RF pulse excitation 110 to the second RF pulse excitation 120, that is, for the first slab 11 to the second slab 12, data of the low frequency phase encoding lines acquired for the first echoes 111 and 121 may be referred to as a first low frequency data set 311. That is, the first low frequency data set 311 may be composed of the first low frequency phase encoding lines 211 to the second low frequency phase encoding lines 212.

Then, for each of the first RF pulse excitation 110 to the second RF pulse excitation 120, that is, for the first slab 11 to the second slab 12, data of the high frequency phase encoding lines acquired for the second echoes 112 and 122 may be referred to as a second high frequency data set 321. That is, the second high frequency data set 321 may be composed of the first high frequency phase encoding lines 221 to the N-th high frequency phase encoding lines 222.

Operation (S120):

For the third RF pulse excitation 130, K-space data for the entire slab 10 may be acquired.

In this case, phase encoding lines corresponding to different frequency domains may be acquired in the plurality of echoes 131 and 132 with respect to the third RF pulse excitation 130. That is, with respect to the third RF pulse excitation 130, third high frequency phase encoding lines 213 may be acquired with respect to a first echo 131 of the plurality of echoes 131 and 132, and third low frequency phase encoding lines 223 may be acquired with respect to the second echo 132. In this case, preferably, the first echo 131 may be an echo that precedes the second echo 132 on the time axis.

Here, with respect to the third RF pulse excitation 130, that is, with respect to the entire slab 10, data of the third high frequency phase encoding lines 213 acquired with respect to the first echo 131 may be referred to as a first high frequency data set 312. Then, with respect to the third RF pulse excitation 130, that is, with respect to the entire slab 10, data of the third low frequency phase encoding lines 223 acquired with respect to the second echo 132 may be referred to as a second low frequency data set 322.

Operation (S130):

The first K-space data 210 may be generated by combining the first low frequency data set 311 and the first high frequency data set 312 with each other and the second K-space data 220 may be generated by combining the second high frequency data set 321 and the second low frequency data set 322 with each other. The first K-space data 210 and the second K-space data 220 generated as described above may be used to generate different images, respectively.

At this time, in the first K-space data 210, the portion indicated by F1 means phase encoding lines acquired for the first slab, the portion indicated by F2 means phase encoding lines acquired for the second slab, and the portion indicated by F1+F2 may mean phase encoding lines acquired for the entire slab including the first slab and the second slab.

Then, in the second K-space data 220, the portion indicated by F1 means phase encoding lines acquired for the first slab, the portion indicated by F2 means phase encoding lines acquired for the second slab, and the portion indicated by F1+F2 may mean phase encoding lines acquired for the entire slab including the first slab and the second slab.

Second Embodiment—Image Processing Method Using Acquired K-Space Data

The image processing method according to the second embodiment of the present invention relates to a technique for generating an image by combining K-space data acquired by the method described above in the first embodiment.

The first type image generated by the image processing method according to the second embodiment of the present invention may be generated by one of the following methods 1 and 2.

Method 1: perform IFFT on the above-described first K-space data to acquire the first type image.

Method 2: (1) perform IFFT on the first low-frequency sub-K-space data consisting of the first low-frequency phase encoding lines to the N-th low-frequency sub-K-space data consisting of the N-th low-frequency phase encoding lines, respectively, to generate a first low frequency sub-image to an N-th low frequency sub-image, (2) perform IFFT on the (N+1)-th high frequency sub K-space data including the (N+1)-th high frequency phase encoding lines to generate an (N+1)-th high frequency sub-image, (3) combining the first low frequency sub-image to the N-th low frequency sub-image and the (N+1)-th high frequency sub-image to generate the first type image.

The second type image generated by the image processing method according to another embodiment of the present invention may be generated by one of the following methods 3 and 4.

Method 3: perform IFFT on the above-described second K-space data to acquire the second type image.

Method 4: (1) perform IFFT on the first high-frequency sub-K-space data consisting of the first high-frequency phase encoding lines to the N-th high-frequency sub-K-space data consisting of the N-th high-frequency phase encoding lines, respectively, to generate a first high frequency sub-image to an N-th high frequency sub-image, (2) perform IFFT on the (N+1)-th low frequency sub K-space data including the (N+1)-th low frequency phase encoding lines to generate an (N+1)-th low frequency sub-image, (3) combining the first high frequency sub-image to the N-th high frequency sub-image and the (N+1)-th low frequency sub-image to generate the second type image.

Third Embodiment—Acquisition of K-Space Data-Generalization

Figure 5:
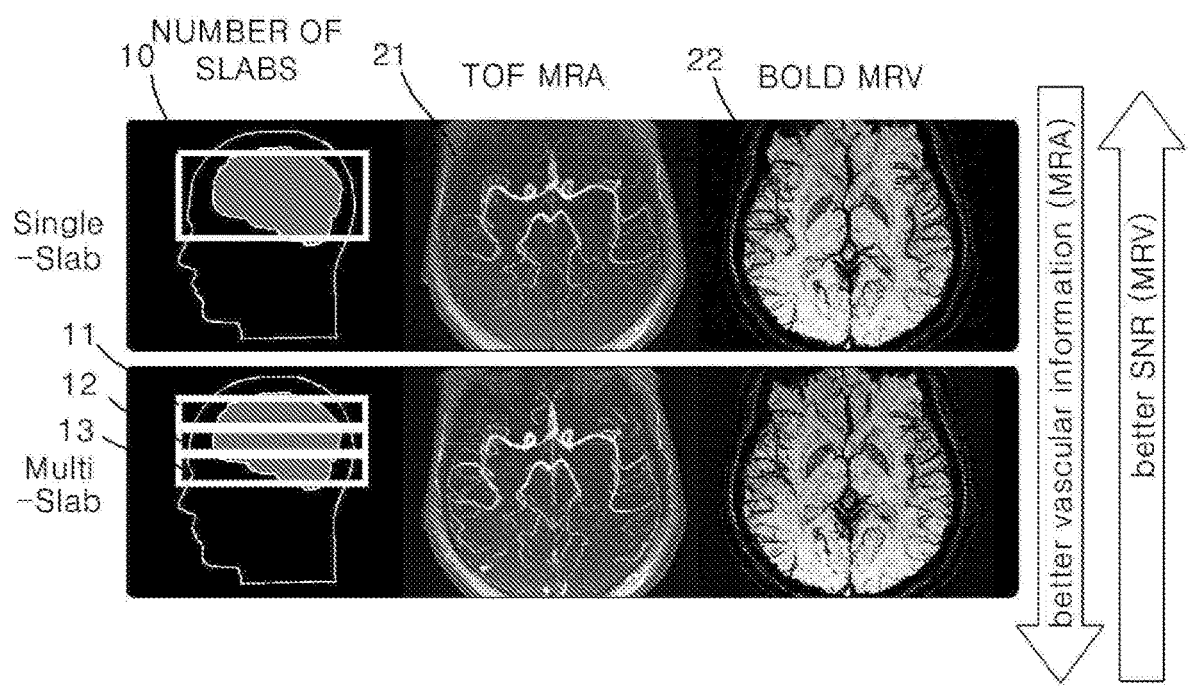
FIG. 5 is a view for explaining a process for acquiring K-space data according to a third embodiment of the present invention.

FIG. 5 is a view for explaining a process for acquiring K-space data according to a third embodiment of the present invention.

Figure 6:
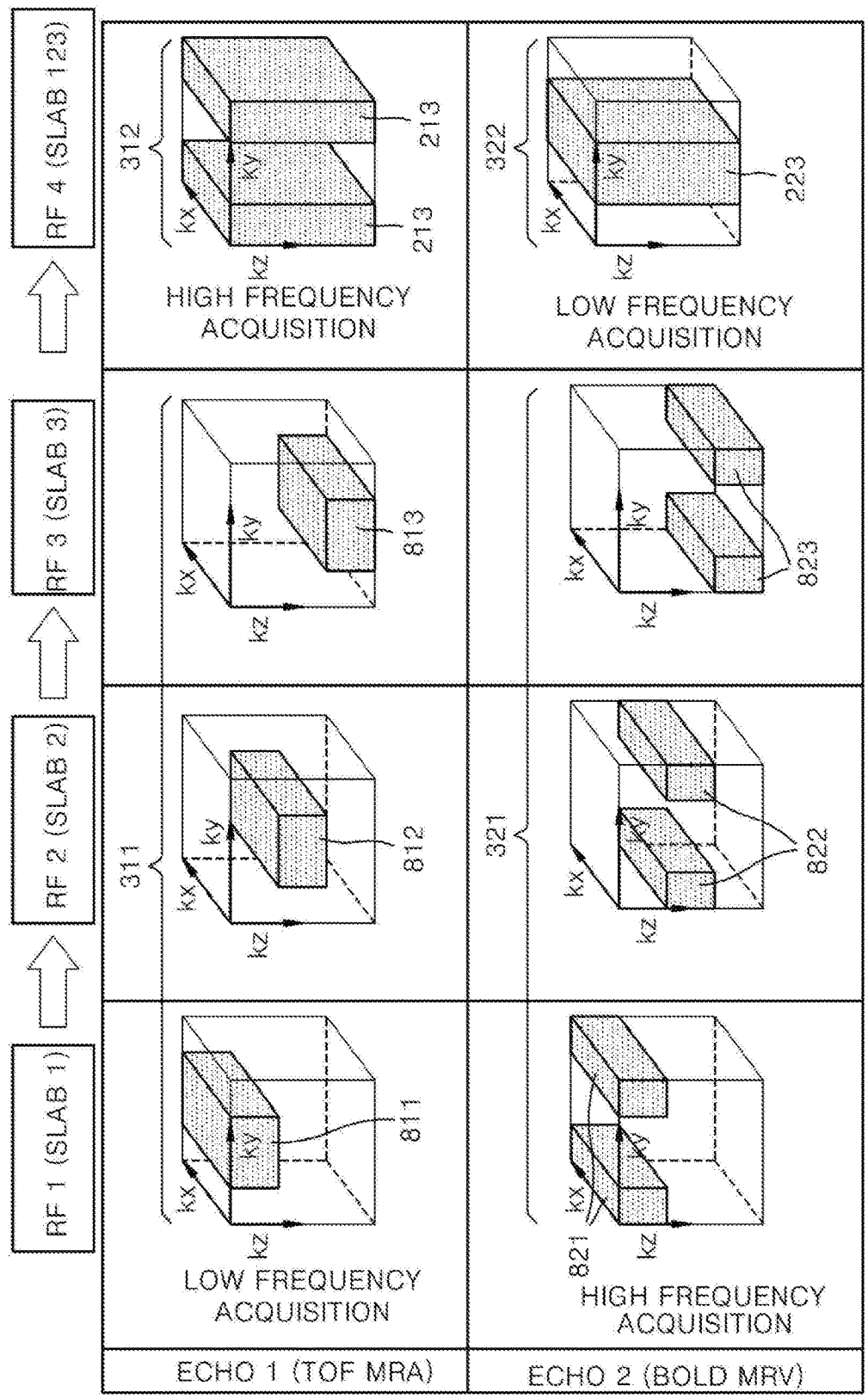
FIG. 6 is a schematic diagram of data acquisition in K-space according to the third embodiment of the present invention.

FIG. 6 is a schematic diagram of data acquisition in K-space according to the third embodiment of the present invention.

In this case, the K-space may mean a 3D space, the x-axis of each K-space may mean time, the y-axis may mean frequency, and the z-axis may mean the height of the slab (e.g., 11).

Figure 7:
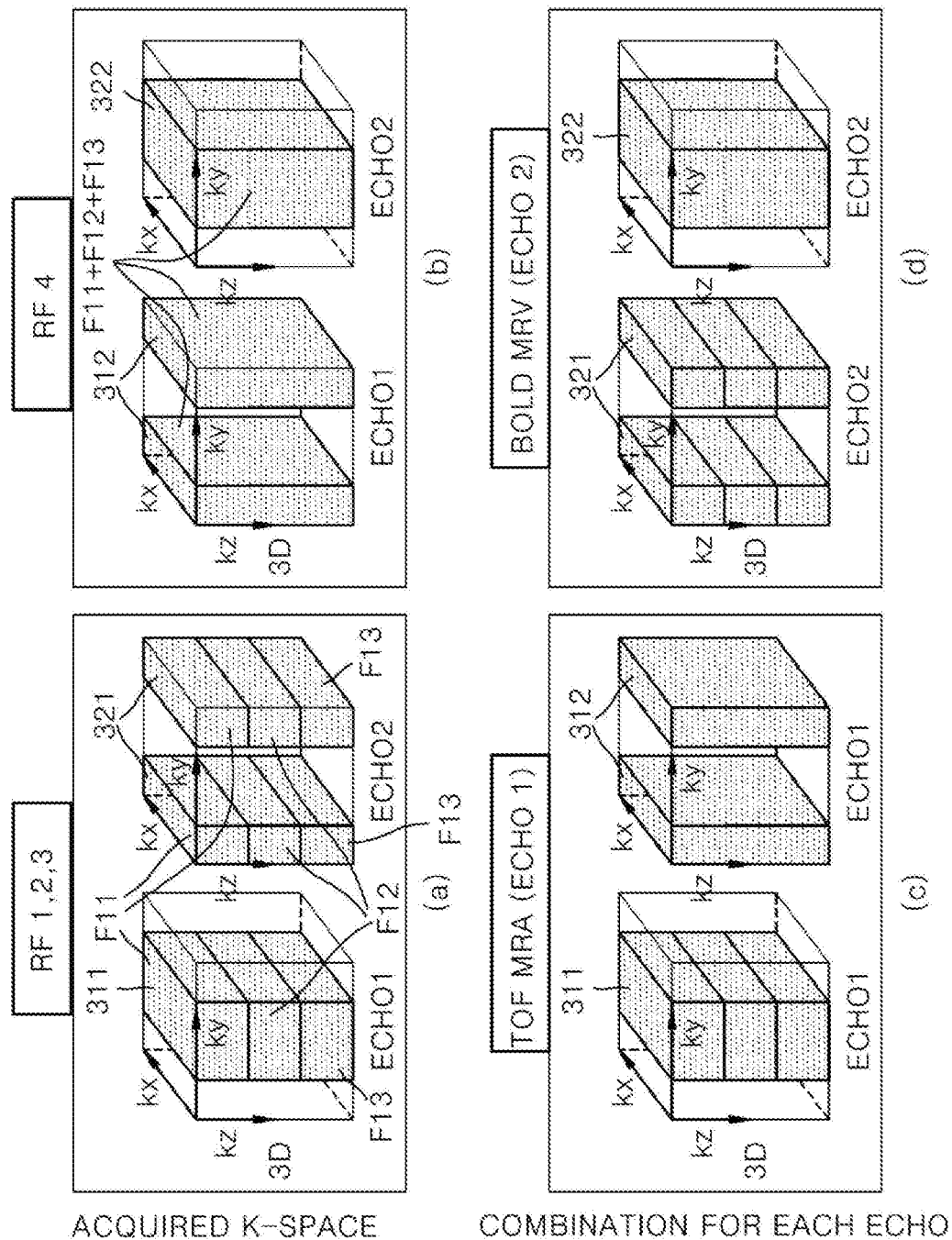
FIG. 7 shows a data structure in K-space according to the third embodiment of the present invention.

FIG. 7 shows a data structure in K-space according to the third embodiment of the present invention. FIG. 7(a) shows the acquired K-spaces for the first RF, the second RF, and the third RF, FIG. 7(b) shows the acquired K-space for the fourth RF, FIG. 7(c) shows a combination of each echo for the TOF MRA, and FIG. 7(d) shows a combination of each echo for the BOLD MRV.

FIGS. 6 and 7 illustrate a case where two echoes (first echo and second echo) are generated for each RF pulse excitation.

However, unlike this, in another embodiment of the present invention, only one echo (first echo) can be generated for each RF pulse excitation, and in this case, the contents related to the second echo among the contents shown in FIGS. 6 and 7 may be removed and presented.

Hereinafter, this will be described with reference to FIGS. 5 and 7.

In order to acquire a set of TOF MRA image 21 and BOLD MRV image 22, the MRI data acquisition target 10 is divided into N slabs (e.g., 11, 12, and 13) and processed. That is, when the MRI data acquisition target 10 is named 'entire slab', the entire slab 10 may include a first slab 11, a second slab 12, a third slab 13, to N slabs that do not overlap each other.

In the K-space data acquisition method according to the third embodiment of the present invention, when the number of slabs to be divided is N (e.g., N=2 or 3), the RF pulse may be generated N+1 times or more. That is, the first RF pulse excitation, the second RF pulse excitation, the third RF pulse excitation, to the (N+1)-th RF pulse excitation may be sequentially performed. For example, when N=2, the first RF pulse excitation 110, the second RF pulse excitation 120, and the third RF pulse excitation 130 may be sequentially performed.

When generalizing the above content, the K-space data acquisition method according to the third embodiment of the present invention may include the following operations.

Operation (S310):

For each of the first RF pulse excitation to the N-th RF pulse excitation 120, K-space data for the first slab (e.g., 11) to the N-th slab (e.g., 13) may be acquired.

In this case, for each of the first RF pulse excitation to the N-th RF pulse excitation, phase encoding lines corresponding to different frequency domains may be acquired in a plurality of echoes. That is, for each of the first RF pulse excitation to the N-th RF pulse excitation (e.g., N=3), first low frequency phase encoding lines (e.g., 811) to N-th low frequency phase encoding lines (e.g., 813) may be acquired with respect to a first echo among the plurality of echoes, and first high frequency phase encoding lines (e.g., 821) to N-th high frequency phase encoding lines (e.g., 823) may be acquired with respect to the second echo. In this case, preferably, the first echo may be an echo preceding in the time axis with respect to the second echo.

Here, for the first RF pulse excitation to the N-th RF pulse excitation, that is, for the first slab (e.g., 11) to the N-th slab (e.g., 13), data of the low frequency phase encoding lines (e.g., 811, 812, and 813) acquired with respect to the first echo may be referred to as a first low frequency data set (e.g., 311). That is, the first low frequency data set may be composed of the first low frequency phase encoding lines to the N-th low frequency phase encoding lines.

Then, for the first RF pulse excitation to the N-th RF pulse excitation, that is, for the first slab (e.g., 11) to the N-th slab (e.g., 13), data of the high frequency phase encoding lines (e.g., 821, 822, and 823) acquired for the second echo may be referred to as a second high frequency data set (e.g., 321). That is, the second high frequency data set may include the first high frequency phase encoding lines to the N-th high frequency phase encoding lines.

In this case, parts indicated by F11, F12, and F13 may mean phase encoding lines acquired for the first slab, phase encoding lines acquired for the second slab, and phase encoding lines acquired for the third slab, respectively.

Operation (S320):

For the (N+1)-th RF pulse excitation 4 (e.g., the fourth RF pulse excitation), K-space data for the entire slab 10 may be acquired.

In this case, phase encoding lines corresponding to different frequency domains may be acquired in the plurality of echoes with respect to the (N+1)-th RF pulse excitation. That is, with respect to the (N+1)-th RF pulse excitation 130, (N+1)-th high frequency phase encoding lines (e.g., 213) may be acquired with respect to a first echo of the plurality of echoes, and (N+1)-th low frequency phase encoding lines (e.g., 223) may be acquired with respect to the second echo. In this case, preferably, the first echo may be an echo preceding in the time axis with respect to the second echo.

Here, with respect to the (N+1)-th RF pulse excitation (e.g., the fourth RF pulse excitation), that is, with respect to the entire slab 10, data of the (N+1)-th high frequency phase encoding lines acquired with respect to the first echo may be referred to as a first high frequency data set (e.g., 312). Then, with respect to the N+1)-th RF pulse excitation, that is, with respect to the entire slab, data of the N+1)-th low frequency phase encoding lines acquired with respect to the second echo may be referred to as a second low frequency data set (e.g., 322).

In this case, a part indicated by F11+F12+F13 may mean phase encoding lines acquired for the entire slab including the first slab, the second slab, and the third slab.

Operation (S330):

The first K-space data may be generated by combining the first low frequency data set (e.g., 311) and the first high frequency data set (e.g., 312) with each other and the second K-space data may be generated by combining the second high frequency data set (e.g., 321) and the second low frequency data set (e.g., 322) with each other. The first K-space data and the second K-space data generated as described above may be used to generate different images, respectively.

Fourth Embodiment—Image Processing Method Using Acquired K-Space Data

The image processing method according to the fourth embodiment of the present invention relates to a technique for generating an image by combining K-space data acquired by the method described above.

The first type image generated by the image processing method according to the second embodiment of the present invention may be generated by one of the following methods 1 and 2.

Method 1: perform IFFT on the above-described first K-space data to acquire the first type image.

Method 2: (1) perform IFFT on the first low-frequency sub-K-space data consisting of the first low-frequency phase encoding lines to the N-th low-frequency sub-K-space data consisting of the N-th low-frequency phase encoding lines, respectively, to generate a first low frequency sub-image to an N-th low frequency sub-image, (2) perform IFFT on the (N+1)-th high frequency sub K-space data including the (N+1)-th high frequency phase encoding lines to generate an (N+1)-th high frequency sub-image, (3) combining the first low frequency sub-image to the N-th low frequency sub-image and the (N+1)-th high frequency sub-image to generate the first type image.

The second type image generated by the image processing method according to another embodiment of the present invention may be generated by one of the following methods 3 and 4.

Method 3: perform IFFT on the above-described second K-space data to acquire the second type image.

Method 4: (1) perform IFFT on the first high-frequency sub-K-space data consisting of the first high-frequency phase encoding lines to the N-th high-frequency sub-K-space data consisting of the N-th high-frequency phase encoding lines, respectively, to generate a first high frequency sub-image to an N-th high frequency sub-image, (2) perform IFFT on the (N+1)-th low frequency sub K-space data including the (N+1)-th low frequency phase encoding lines to generate an (N+1)-th low frequency sub-image, (3) combining the first high frequency sub-image to the N-th high frequency sub-image and the (N+1)-th low frequency sub-image to generate the second type image.

Fifth Embodiment

A fifth embodiment of the present invention relates to a method of acquiring an image (data) using a plurality of echoes.

Hereinafter, this will be described with reference to FIGS. 1 and 4.

The data acquisition method may include the following procedure.

The first process of exciting the first RF 110 that excites only the first slab 11 among the plurality of slabs 11 and 12 a plurality of times may be performed. At this time, each time exciting the first RF 110, in the first echo 111, the low frequency components 211 may be acquired according to a predetermined order, and in the second echo 112, the high frequency components 221 may be acquired according to a predetermined order.

After the first process, a second process of exciting the second RF 120 that excites only the second slab 12 of the plurality of slabs a plurality of times may be performed. At this time, each time exciting the second RF 120, in the first echo 121, the low frequency components 212 may be acquired according to a predetermined order, and in the second echo 122, the high frequency components 222 may be acquired according to a predetermined order.

After the second process, a third process of a plurality of times exciting the third RF 130 for exciting the entire slab 10 at once may be performed. In this case, each time exciting the third RF 130, the first echo 131 acquires the high frequency component 213 according to a predetermined order, and the second echo 132 acquires the low frequency component 223 according to a predetermined order.

Table 1 below shows the frequency bands that can be acquired for each excitation target.

TABLE 1

| Excitation target | Acquired frequency band | Acquired frequency band |
| --- | --- | --- |
| First slab | Low frequency 211 | High frequency 221 |
| Second slab | Low frequency 212 | High frequency 222 |
| Entire | High frequency 213 | Low frequency 223 |

Figure 8:
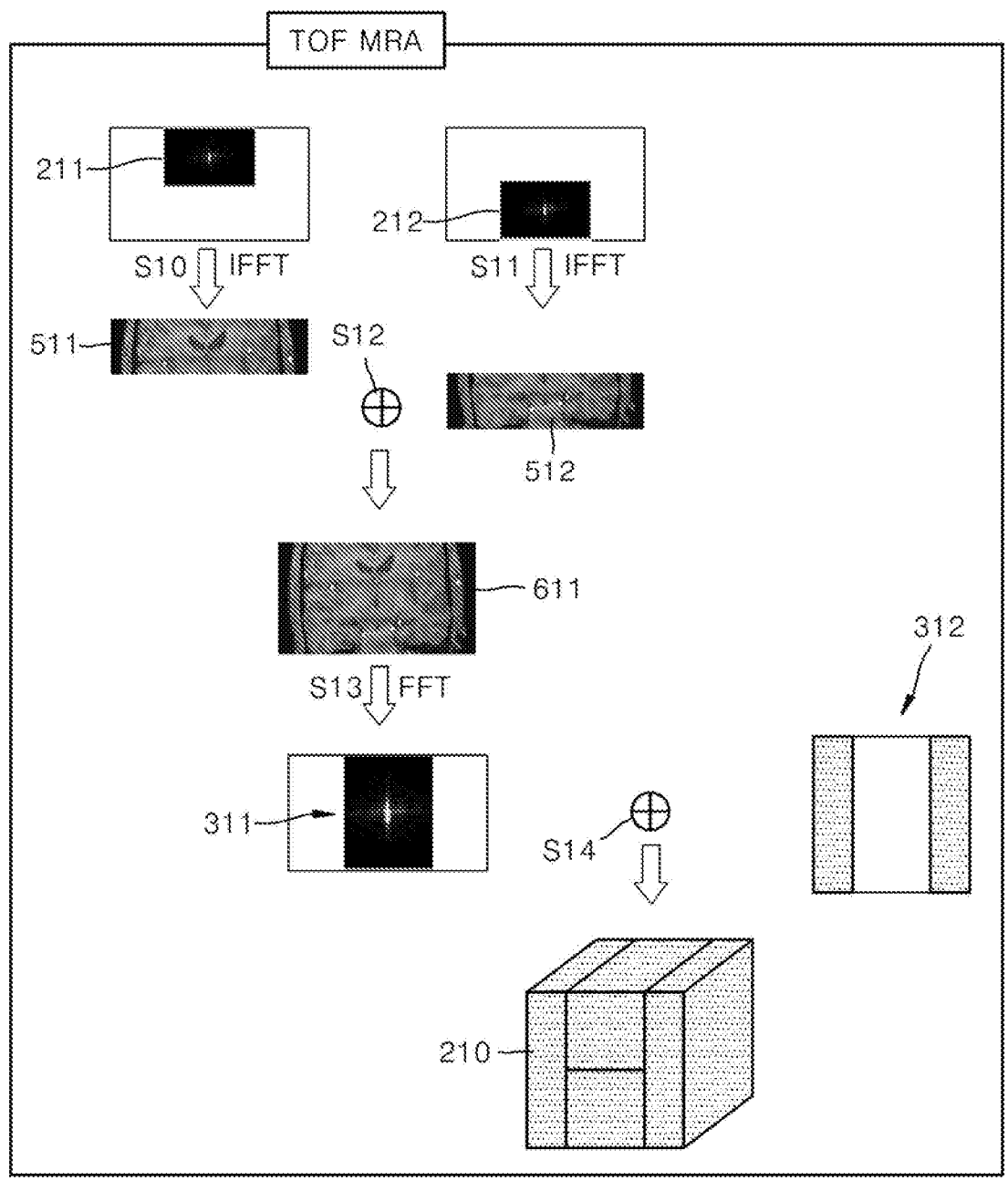
FIG. 8 is a diagram for describing an image processing method for acquiring a TOF MRA image according to a fifth embodiment of the present invention.

FIG. 8 is a diagram for describing an image processing method for acquiring a TOF MRA image according to a fifth embodiment of the present invention.

In operation S10, the first low-frequency phase encoding lines 211 acquired by the first echoes 111 of the first process are transformed (IFFT) into an image region to generate the first low-frequency sub-image 511.

In operation S11, the second low-frequency phase encoding lines 212 acquired by the first echoes 121 of the second process are transformed (IFFT) into an image region to generate the second low-frequency sub-image 512.

In operation S12, a third low frequency sub-image 611 may be generated by combining the first low frequency sub-image 511 and the second low frequency sub-image 512.

In operation S13, the first low frequency data set 311 may be acquired by transforming (FFT) the third low frequency sub-image 611 into a frequency domain.

In operation S14, the first low frequency data set 311 and the third high frequency phase encoding lines 312 acquired from the first echoes 131 of the third process are combined with each other in a frequency domain, thereby acquiring the first K-space data 210.

Figure 9:
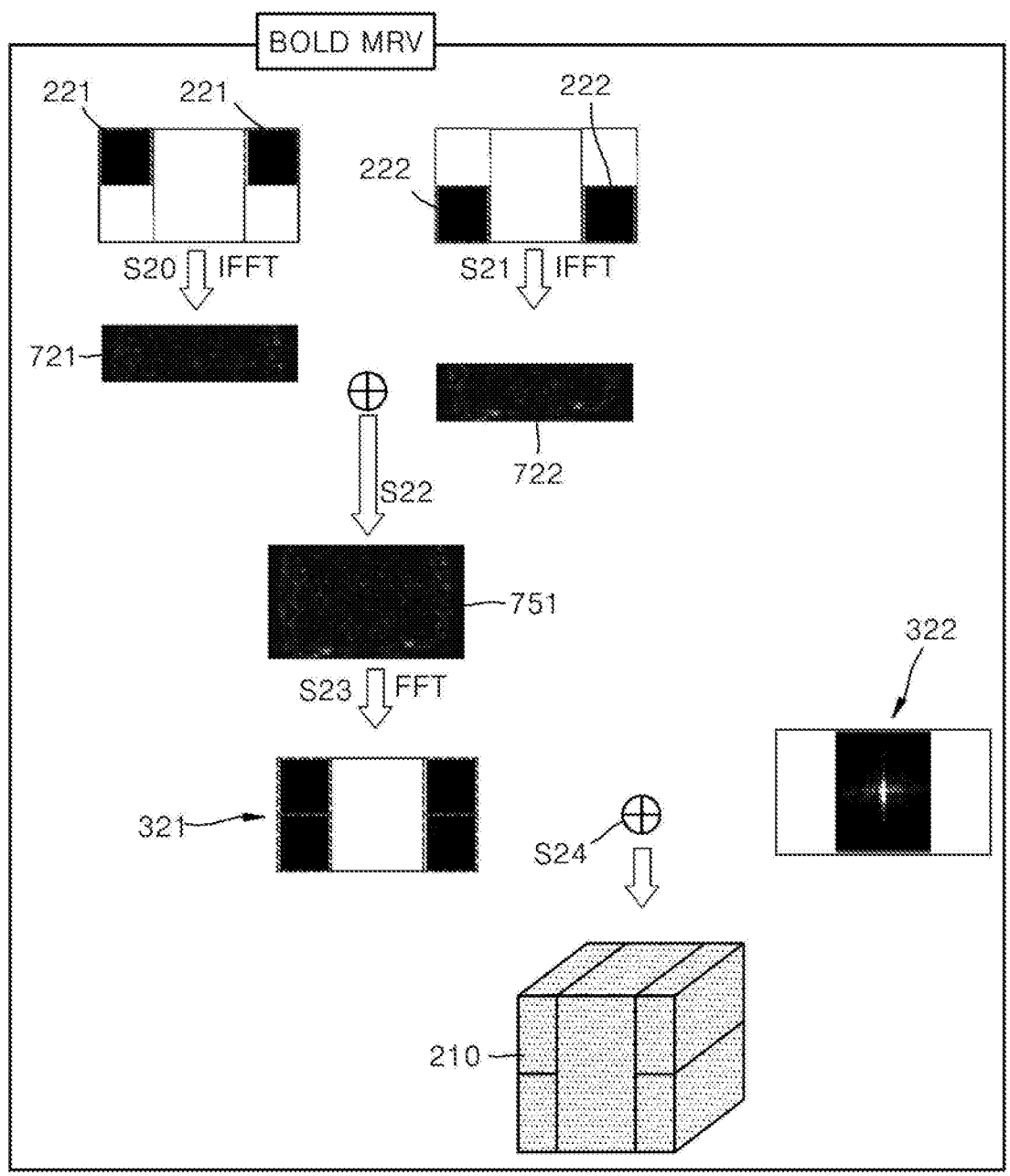
FIG. 9 is a diagram for describing an image processing method for acquiring a BOLD MRV image according to a fifth embodiment of the present invention.

FIG. 9 is a diagram for describing an image processing method for acquiring a BOLD MRV image according to a fifth embodiment of the present invention.

In operation S20, the first high-frequency phase encoding lines 221 acquired by the second echoes 112 of the first process are transformed into an image region to generate the first high-frequency sub-image 721.

In operation S21, the second high-frequency phase encoding lines 222 acquired by the second echoes 122 of the second process are transformed into an image region to generate the second high-frequency sub-image 722.

In operation S22, a third high frequency sub-image 751 may be generated by combining the first high frequency sub-image 721 and the second high frequency sub-image 722.

In operation S23, the second high frequency data set 321 may be acquired by transforming (FFT) the third high frequency sub-image 751 into a frequency domain.

In operation S24, the second high frequency data set 321 and the third low frequency phase encoding lines 322 acquired from the second echoes 132 of the third process are combined with each other in a frequency domain, thereby acquiring the second K-space data 220.

The method of acquiring the TOF MRA and BOLD MRV image described above with reference to FIGS. 8 to 9 may be a method for acquiring the image at high speed.

Unlike the above description, the method of acquiring the TOF MRA image and the BOLD MRV image at a normal speed may include the following process.

First, in the case of a TOF MRA image, first low frequency phase encoding lines 211 acquired from the first echoes of the first process, second low frequency phase encoding lines 212 acquired from the first echoes of the second process, and the third high frequency phase encoding lines 213 acquired from the first echoes of the third process are transformed into image regions, respectively, thereby combining them with each other in the image region.

In the case of a BOLD MRV image, first high frequency phase encoding lines 221 acquired from the second echoes of the first process, second high frequency phase encoding lines 222 acquired from the second echoes of the second process, and the third low frequency phase encoding lines 223 acquired from the second echoes of the third process are transformed into image regions, respectively, thereby combining them with each other in the image region.

In the fifth embodiment, shooting conditions in the first echoes 111, 121, and 131 and shooting conditions in the second echoes 112, 122, and 132 may be different from each other.

In addition, the first echoes 111, 121, and 131 may precede the second echoes 112, 122, and 132. In this case, a Time of Flight MR angiogram may be acquired at the time of the first echo, and susceptibility weighted imaging may be acquired at the time of the second echo.

In addition, the number of slabs in the first echoes 111, 121, and 131 may be greater than the number of slabs in the second echoes 112, 122, and 132.

Then, as described above with reference to FIGS. 8 and 9, arterial images may be acquired during the first echoes 111, 121, and 131, and venous images 112, 122, and 132 are acquired during the second echoes.

Sixth Embodiment

The sixth embodiment relates to another method of acquiring a TOF MRA image and a BOLD MRV image. The sixth embodiment may correspond to the case where N=3 in the above-described third embodiment.

Figure 10:
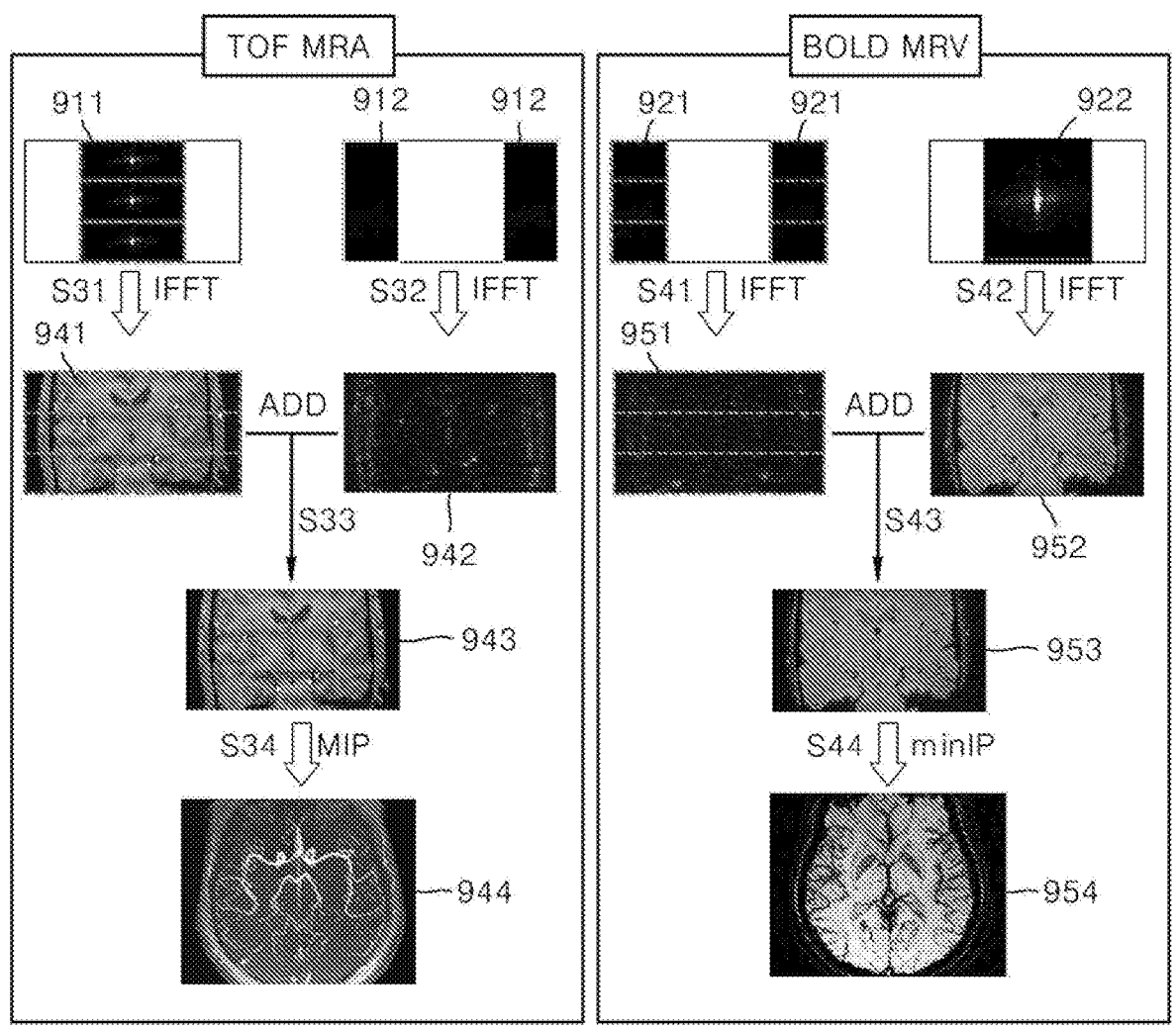
FIG. 10 is a diagram for describing an image processing method for acquiring a TOF MRA image and a BOLD MRV image according to a sixth embodiment of the present invention.

FIG. 10 is a diagram for describing an image processing method for acquiring a TOF MRA image and a BOLD MRV image according to a sixth embodiment of the present invention.

FIG. 10($a$) illustrates an image processing procedure for the TOF MRA, and FIG. 10($b$) illustrates an image processing procedure for the BOLD MRV.

In operation S31, the low frequency phase encoding lines acquired in the respective first echoes of the first slab 11, the second slab 12, and the third slab 13 are transformed (IFFT) into an image region, respectively, to generate a first low frequency image 941. In this case, the first low frequency image 941 may be acquired by disposing and combining low frequency sub-images acquired through transformation into the respective image regions according to positions of the slabs 11, 12, and 13.

In operation S32, the first high frequency image 942 may be generated by transforming (IFFT) the high frequency phase encoding lines 912 acquired from the first echoes of the entire slab 10 into an image region.

In operation S33, a first entire image 943 may be generated by combining the first low frequency image 941 and the second low frequency image 942.

In operation S34, a TOF MRA image 944 may be acquired by performing a Maximum Intensity Projection (MIP) on the first entire image 943.

Next, a method of acquiring a BOLD MRV image is as follows.

In operation S41, the high frequency phase encoding lines acquired in the respective second echoes of the first slab 11, the second slab 12, and the third slab 13 are transformed (IFFT) into an image region, respectively, to generate a second high frequency image 951. In this case, the first high frequency image 951 may be acquired by disposing and combining low frequency sub-images acquired through transformation into the respective image regions according to positions of the slabs 11, 12, and 13.

In operation S42, the second low frequency image 952 may be generated by transforming (IFFT) the low frequency phase encoding lines 922 acquired from the second echoes of the entire slab 10 into an image region.

In operation S43, a second entire image 953 may be generated by combining the second high frequency image 951 and the second low frequency image 952.

In operation S44, the BOLD MRV image 954 may be acquired by performing phase mask filtering and Minimum Intensity Projection (minIP) on the second entire image 953.

Seventh Embodiment

The seventh embodiment relates to another data acquisition method using a plurality of echoes.

According to the data acquisition method, first, for each of the first echo 111 and the second echo 112 generated by exciting the first RF signal 110 with respect to the first slab 11, low-frequency lines 211 and high-frequency lines 221 of the K-space lines may be acquired.

Then, for each of the third echo 121 and the fourth echo 122 generated by exciting the second RF signal 120 with respect to the second slab 12, the low frequency lines 212 and the high frequency lines 222 of the K-space lines may be acquired.

Then, for the entire slab 10 including the first slab 11 and the second slab 12, the high frequency lines 213 are acquired in the fifth echo 131 generated by exciting the third RF signal 130, and the low frequency lines 223 may be acquired in the sixth echo 132.

In this case, the first echo may precede the second echo, or the second echo may precede the first echo.

Eighth Embodiment

The eighth embodiment relates to another data acquisition method using a plurality of echoes.

According to the data acquisition method, first, for each of the first slab 11 and the second slab 12, some lines 211 and 212 according to the first ordering are acquired in the first echoes 111 and 121, and some lines 221 and 222 according to the second ordering may be acquired in the second echoes 112 and 122.

And, for the entire slab 10, the first echo 131 may acquire at least some of the remaining lines 213 according to the first ordering, and the second echo 132 may acquire at least some of the remaining lines 223 according to the second ordering.

Ninth Embodiment

The ninth embodiment relates to another data acquisition method using a plurality of echoes.

According to the data acquisition method, some lines 211 and 212 according to the first ordering may be acquired for each of the first slab 11 and the second slab 12. Then, the remaining lines 213 according to the first ordering may be acquired with respect to the entire slab 10. Thereafter, information on the some lines and the remaining lines may be combined with each other.

Tenth Embodiment

The tenth embodiment relates to another data acquisition method using a plurality of echoes.

According to the data acquisition method, for each of the plurality of slabs 11 and 12 defined by dividing the entire slab 10, the low frequency lines 211 and 212 may be acquired in the first echoes 111 and 121, and the high frequency lines 221 and 222 may be acquired in the second echoes 112 and 122. And, for the entire slab 10, the first echo 131 may acquire the high frequency line 213 and the second echo 132 may acquire the low frequency line 223.

Figure 11A:
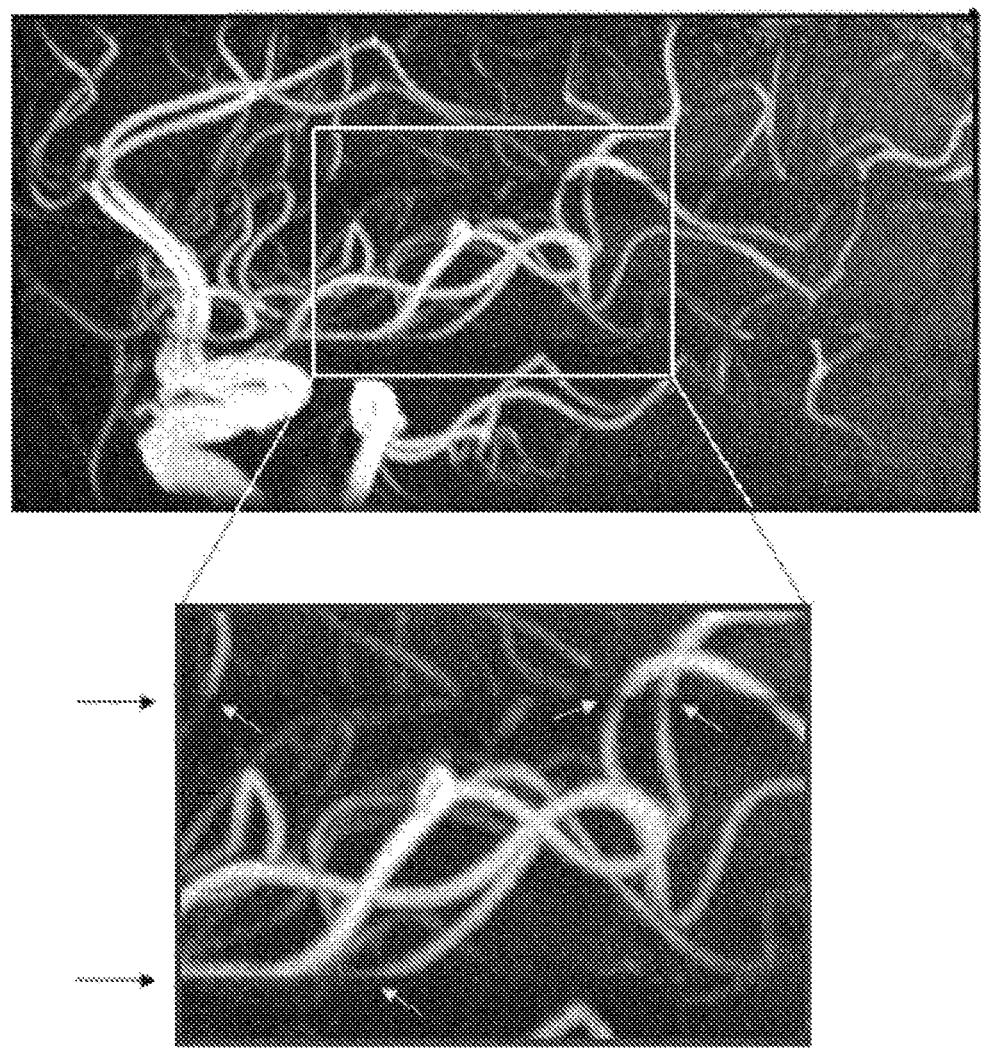
FIG. 11A is an arteriogram acquired when the observation target is divided into three slabs according to a conventional technique.
Figure 11B:
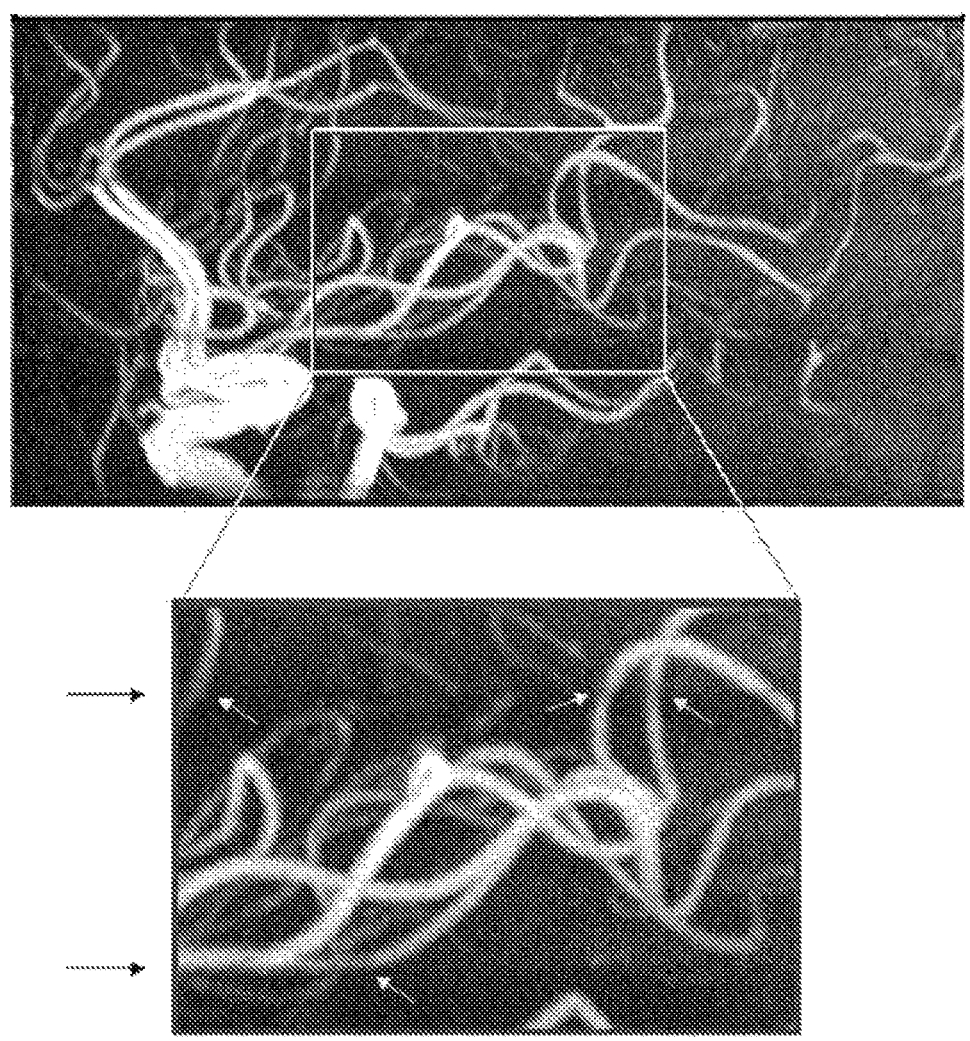
FIG. 11B is an arteriogram acquired when the observation object is divided into three slabs according to an embodiment of the present invention.

FIG. 11A and FIG. 11B illustrate a difference between an image acquired according to a TOF MRA using an embodiment of the present invention and an image acquired according to a TOF MRA according to the related art.

FIG. 11A is an arteriogram acquired when the observation target is divided into three slabs according to a conventional technique. Referring to FIG. 11A, it can be seen that an artifact in the form of a horizontal line appears at a boundary portion (arrow mark) between slabs.

FIG. 11A is an arteriogram acquired when the observation object is divided into three slabs according to an embodiment of the present invention. Referring to FIG. 11B, it can be seen that an artifact in the form of a horizontal line does not appear at a boundary portion (arrow mark) between slabs. That is, it can be understood that the image of FIG. 11B is improved compared to the image of FIG. 11A. Therefore, when using the method according to an embodiment of the present invention, it can be seen that the quality of the arteriogram is improved compared to the prior art.

The improvement of the arteriogram can be acquired even when using multiple echoes in the embodiment according to the present invention, and even when using a single echo. That is, in addition to the case of using both the first echo and the second echo as in the embodiment of the present invention described with reference to FIGS. 3 and 4, in a case of using only the first echo without using the second echo, it is possible to acquire a quality improvement of the arteriogram. In addition, in addition to the case of using both the first echo and the second echo as in the embodiment of the present invention described with reference to FIGS. 6 and 7, in a case of using only the first echo without using the second echo, it is possible to acquire a quality improvement of the arteriogram.

In order to explain the effect according to the present invention, the effect in the application to acquire an arteriogram has been presented but improved effects can be acquired by applying the present invention to other applications.

Eleventh Embodiment

The eleventh embodiment relates to another data acquisition method using one or more echoes.

Figure 12:
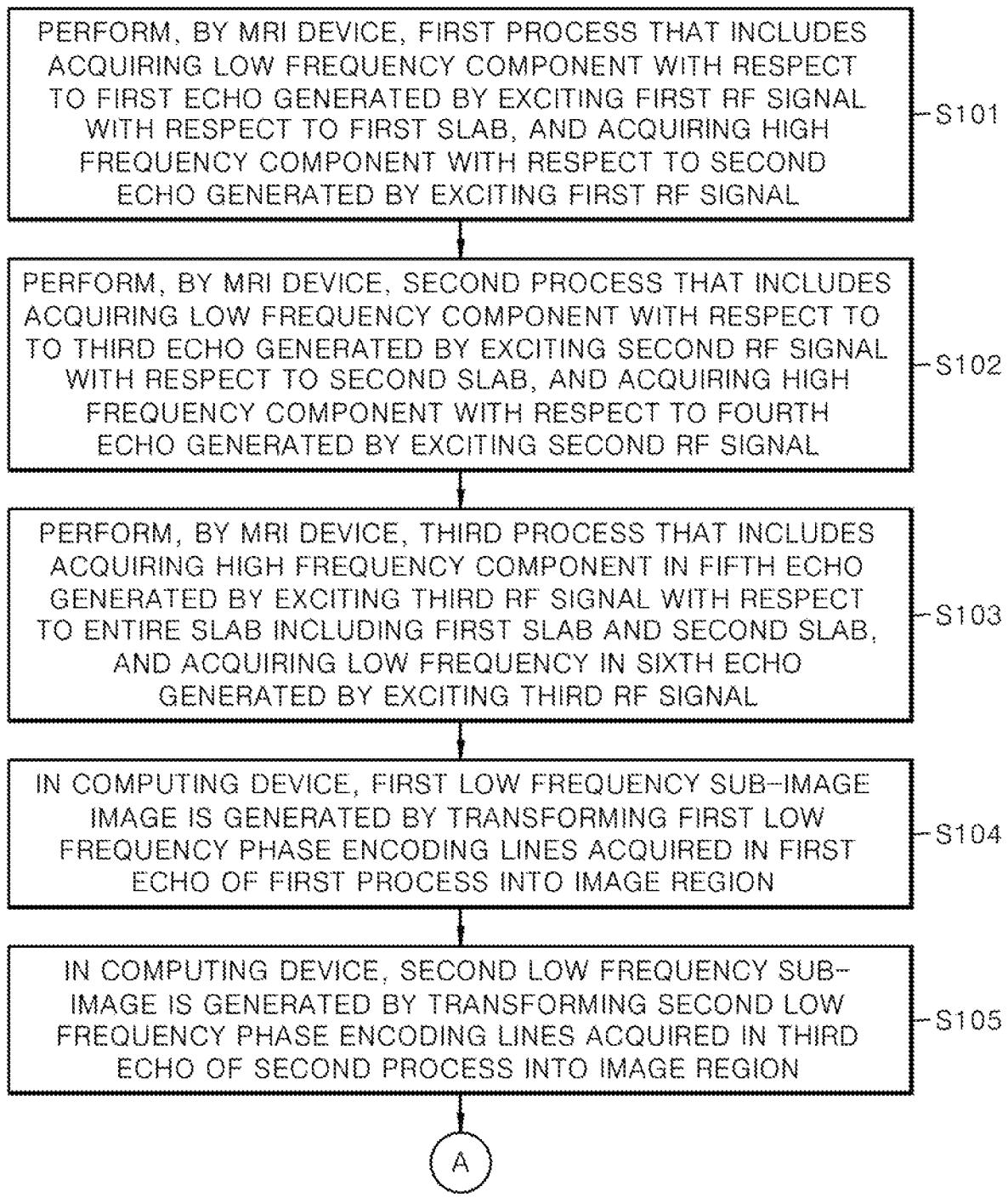
FIG. 12 is a flowchart illustrating a data acquisition method according to an eleventh embodiment of the present invention.
Figure 12:
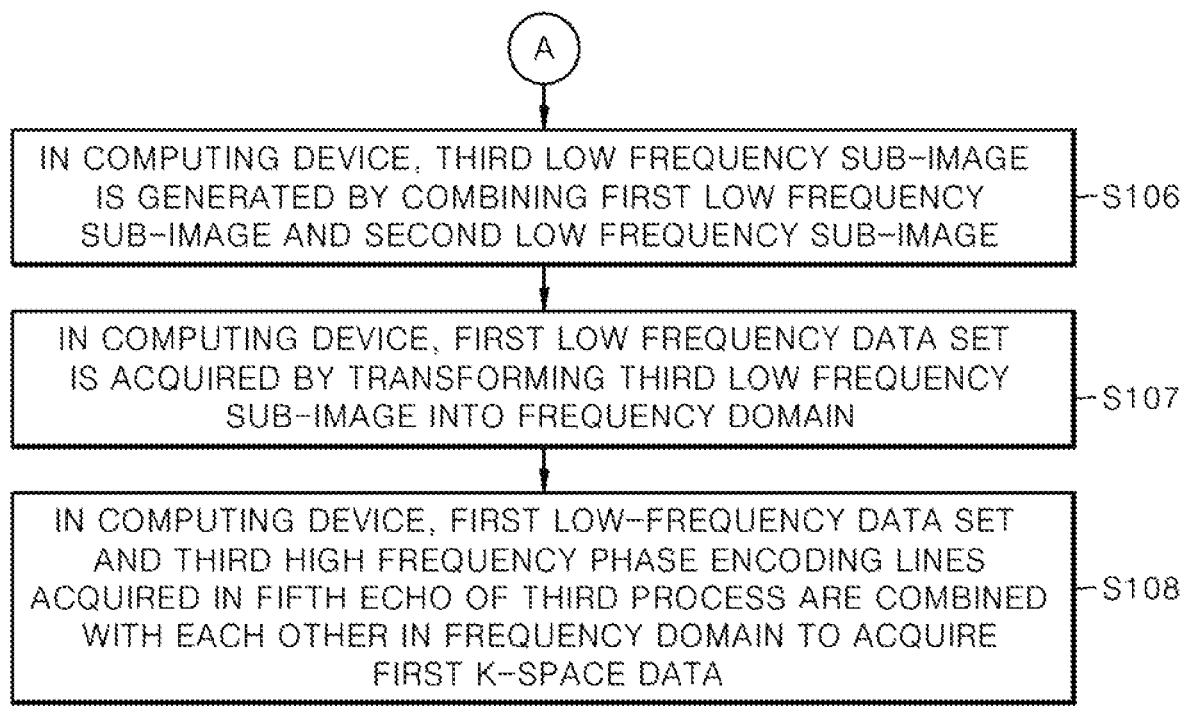

FIG. 12 is a flowchart illustrating a data acquisition method according to an eleventh embodiment of the present invention.

In operation S101, the MRI device may perform a first process that includes acquiring a low frequency component with respect to the first echo generated by exciting the first RF signal with respect to the first slab, and acquiring a high frequency component with respect to the second echo generated by exciting the first RF signal.

In operation S102, the MRI device may perform a second process that includes acquiring a low frequency component with respect to the third echo generated by exciting the second RF signal with respect to the second slab, and acquiring a high frequency component with respect to the fourth echo generated by exciting the second RF signal.

In operation S103, the MRI device may perform a third process that includes acquiring a high frequency component in a fifth echo generated by exciting a third RF signal with respect to the entire slab including the first slab and the second slab, and acquiring a low frequency in a sixth echo generated by exciting the third RF signal.

In operation S104, in a computing device, the first low frequency sub-image may be generated by transforming the first low frequency phase encoding lines acquired in the first echo of the first process into an image region.

In operation S105, in a computing device, the second low frequency sub-image may be generated by transforming the second low frequency phase encoding lines acquired in the third echo of the second process into an image region.

In operation S106, in the computing device, a third low frequency sub-image may be generated by combining the first low frequency sub-image and the second low frequency sub-image.

In operation S107, in the computing device, a first low frequency data set may be acquired by transforming the third low frequency sub-image into a frequency domain.

In operation S108, in the computing device, the first low-frequency data set and the third high frequency phase encoding lines acquired in the fifth echo of the third process are combined with each other in a frequency domain to acquire the first K-space data.

In this case, the first echo may be an echo generated earlier than the second echo, the third echo may be an echo generated earlier than the fourth echo, and the fifth echo may be an echo generated earlier than the sixth echo.

In this case, the first echo may be the first echo generated by exciting the first RF signal, the second echo may be the second echo generated by exciting the first RF signal, the third echo may be the first echo generated by exciting the second RF signal, the fourth echo may be the second echo generated by exciting the second RF signal, the fifth echo may be the first echo generated by exciting the third RF signal, and the sixth echo may be the second echo generated by exciting the third RF signal.

That is, for the first slab, some lines may be acquired according to the first ordering in the first echo, and some lines may be acquired according to the second ordering in the second echo. And, for the second slab, some lines may be acquired according to the third ordering in the third echo and some lines may be acquired according to the fifth ordering in the fourth echo. And, for the entire slab, at least some of the remaining lines according to the fifth ordering may be acquired in the fifth echo, and at least some of the remaining lines according to the sixth ordering may be acquired in the sixth echo.

In other words, the first process is to excite the first RF a plurality of times, and each time the first RF is excited, the first echo may be configured to acquire low frequency lines among K-space lines according to a predetermined order. Then, the second echo may be configured to acquire high frequency lines among K-space lines according to a predetermined order.

In addition, the second process is to excite the second RF a plurality of times, and each time the second RF is excited, the third echo may be configured to acquire low frequency lines among K-space lines according to a predetermined order. Then, the fourth echo may be configured to acquire high frequency lines among K-space lines according to a predetermined order.

In addition, the third process is to excite the third RF a plurality of times, and each time the third RF is excited, the fifth echo may be configured to acquire high frequency lines among K-space lines according to a predeteimined order. Then, the sixth echo may be configured to acquire low frequency lines among K-space lines according to a predetermined order.

In this case, the shooting conditions in the first echo and the shooting conditions in the second echo may be different.

In addition, a Time of Flight MR angiogram may be acquired at the time of the first echo, and susceptibility weighted imaging may be acquired at the time of the second echo.

In addition, the arterial image is acquired by using the data acquired in the first echo, the third echo, and the fifth echo, and the venous image may be acquired by using data acquired in the second echo, the fourth echo, and the sixth echo.

Twelfth Embodiment

The twelfth embodiment relates to another data acquisition method.

Figure 13:
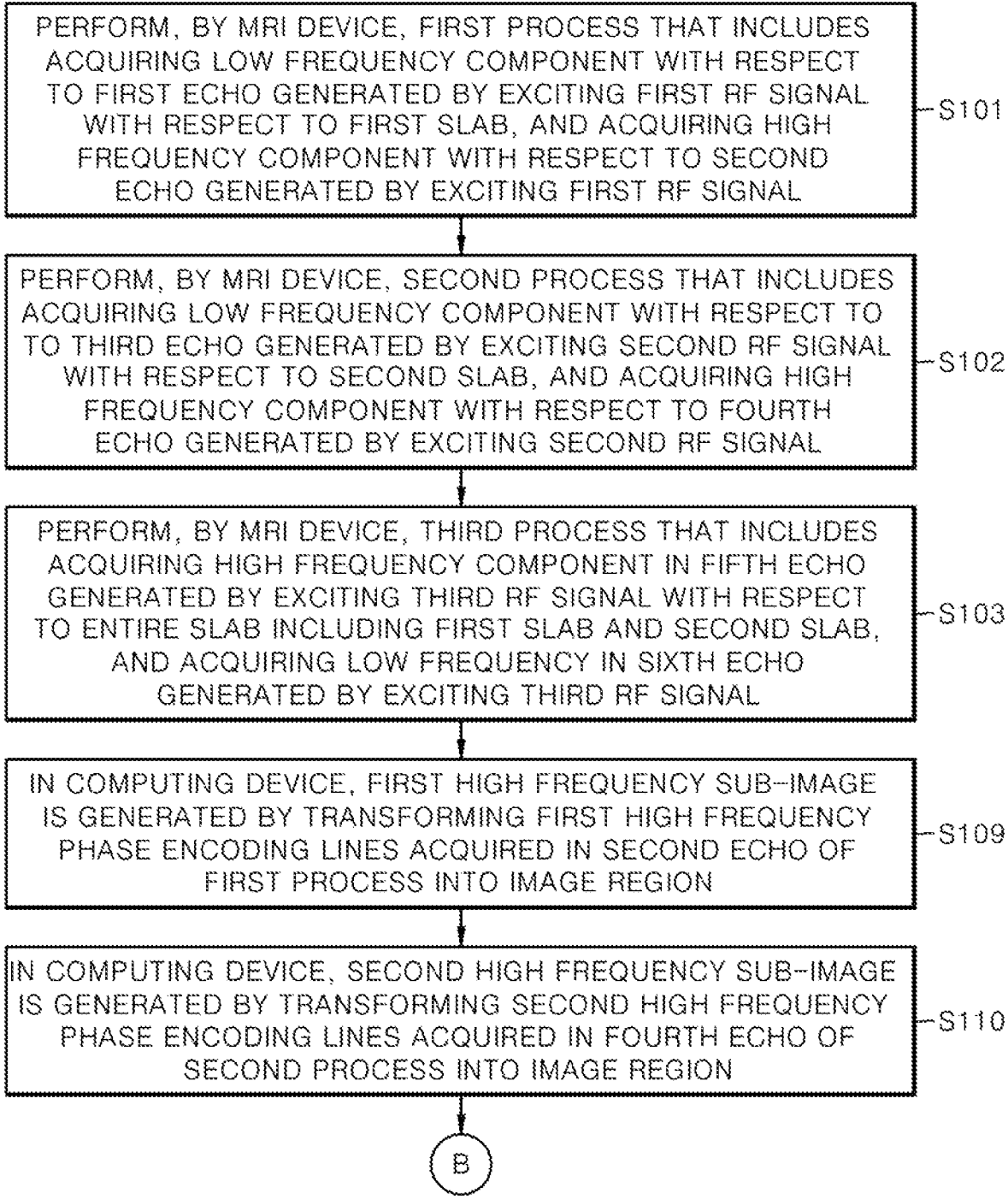
FIG. 13 is a flowchart illustrating a data acquisition method according to a twelfth embodiment of the present invention.
Figure 13:
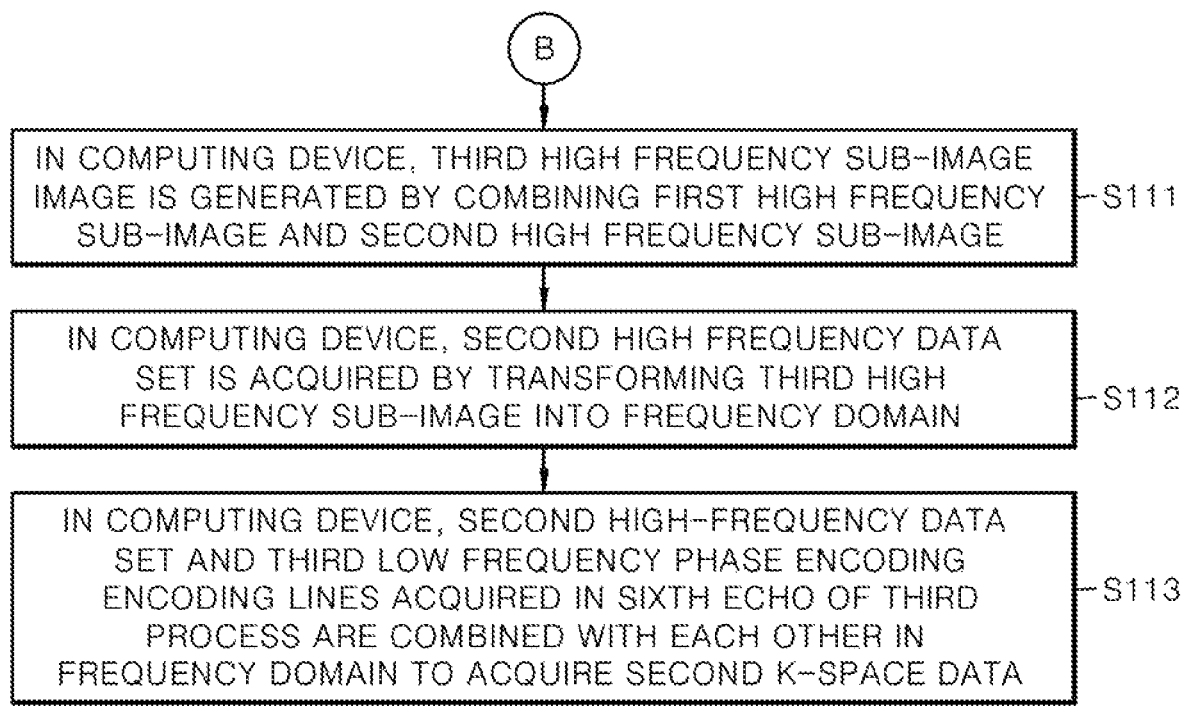

FIG. 13 is a flowchart illustrating a data acquisition method according to a twelfth embodiment of the present invention.

In operation S101, the MRI device may perform a first process that includes acquiring a low frequency component with respect to the first echo generated by exciting the first RF signal with respect to the first slab, and acquiring a high frequency component with respect to the second echo generated by exciting the first RF signal.

In operation S102, the MRI device may perform a second process that includes acquiring a low frequency component with respect to the third echo generated by exciting the second RF signal with respect to the second slab, and acquiring a high frequency component with respect to the fourth echo generated by exciting the second RF signal.

In operation S103, the MRI device may perform a third process that includes acquiring a high frequency component in a fifth echo generated by exciting a third RF signal with respect to the entire slab including the first slab and the second slab, and acquiring a low frequency in a sixth echo generated by exciting the third RF signal.

In operation S109, in a computing device, a first high frequency sub-image may be generated by transforming first high frequency phase encoding lines acquired in the second echo of the first process into an image region.

In operation S110, in a computing device, a second high frequency sub-image may be generated by transforming second high frequency phase encoding lines acquired in the fourth echo of the second process into an image region.

In operation S111, in the computing device, a third high frequency sub-image may be generated by combining the first high frequency sub-image and the second high frequency sub-image.

In operation S112, in the computing device, a second high frequency data set may be acquired by transforming the third high frequency sub-image into a frequency domain.

In operation S113, in the computing device, the second high-frequency data set and the third low frequency phase encoding lines acquired in the sixth echo of the third process are combined with each other in a frequency domain to acquire the second K-space data.

Thirteenth Embodiment

The thirteenth embodiment relates to another data acquisition method.

Figure 14:
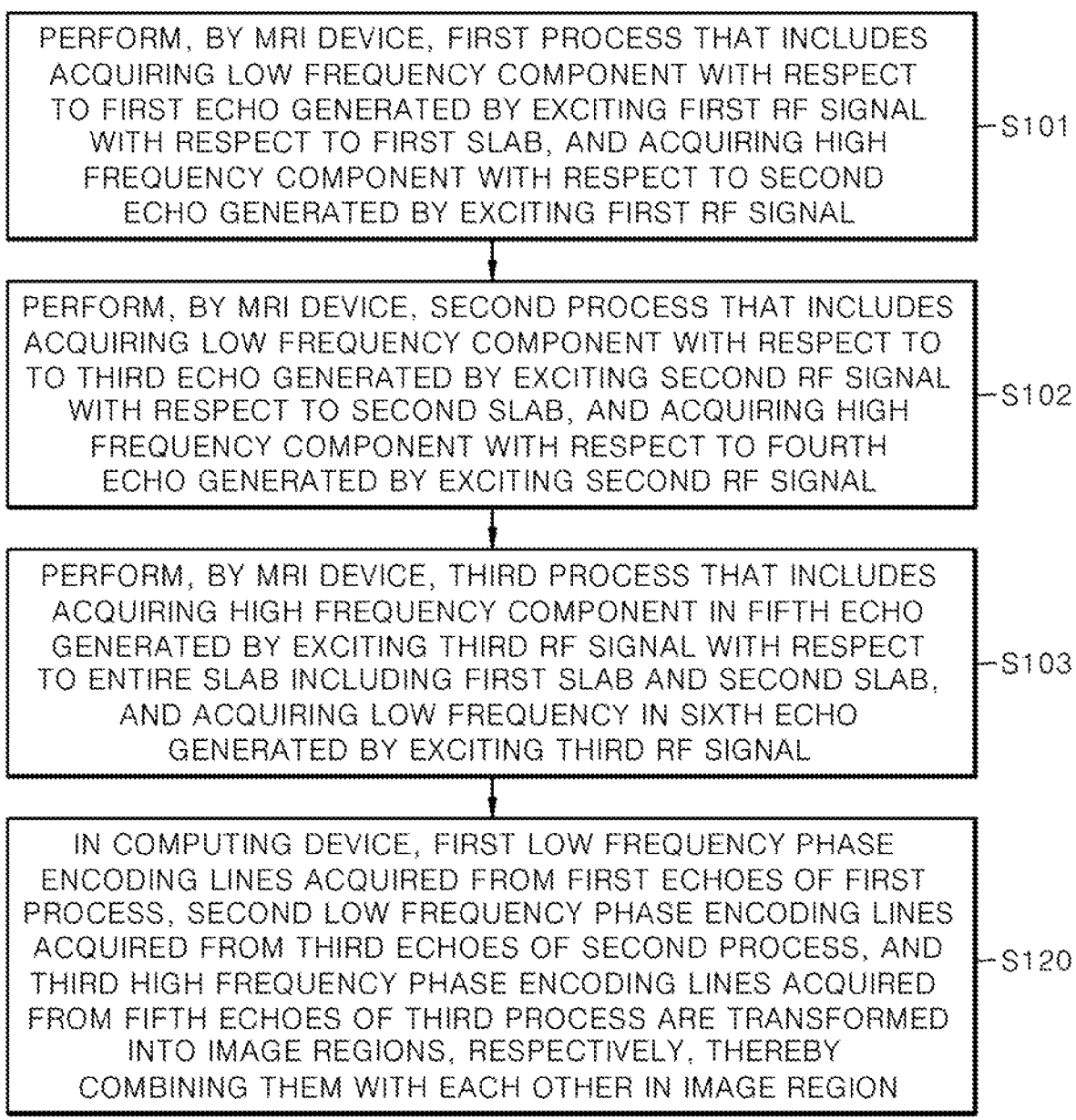
FIG. 14 is a flowchart illustrating a data acquisition method according to a thirteenth embodiment of the present invention.

FIG. 14 is a flowchart illustrating a data acquisition method according to a thirteenth embodiment of the present invention.

In operation S101, the MRI device may perform a first process that includes acquiring a low frequency component with respect to the first echo generated by exciting the first RF signal with respect to the first slab, and acquiring a high frequency component with respect to the second echo generated by exciting the first RF signal.

In operation S102, the MRI device may perform a second process that includes acquiring a low frequency component with respect to the third echo generated by exciting the second RF signal with respect to the second slab, and acquiring a high frequency component with respect to the fourth echo generated by exciting the second RF signal.

In operation S103, the MRI device may perform a third process that includes acquiring a high frequency component in a fifth echo generated by exciting a third RF signal with respect to the entire slab including the first slab and the second slab, and acquiring a low frequency in a sixth echo generated by exciting the third RF signal.

In operation S120, in the computing device, first low frequency phase encoding lines acquired from the first echoes of the first process, second low frequency phase encoding lines acquired from the third echoes of the second process, and the third high frequency phase encoding lines acquired from the fifth echoes of the third process are transformed into image regions, respectively, thereby combining them with each other in the image region.

Fourteenth Embodiment

The fourteenth embodiment relates to another data acquisition method.

Figure 15:
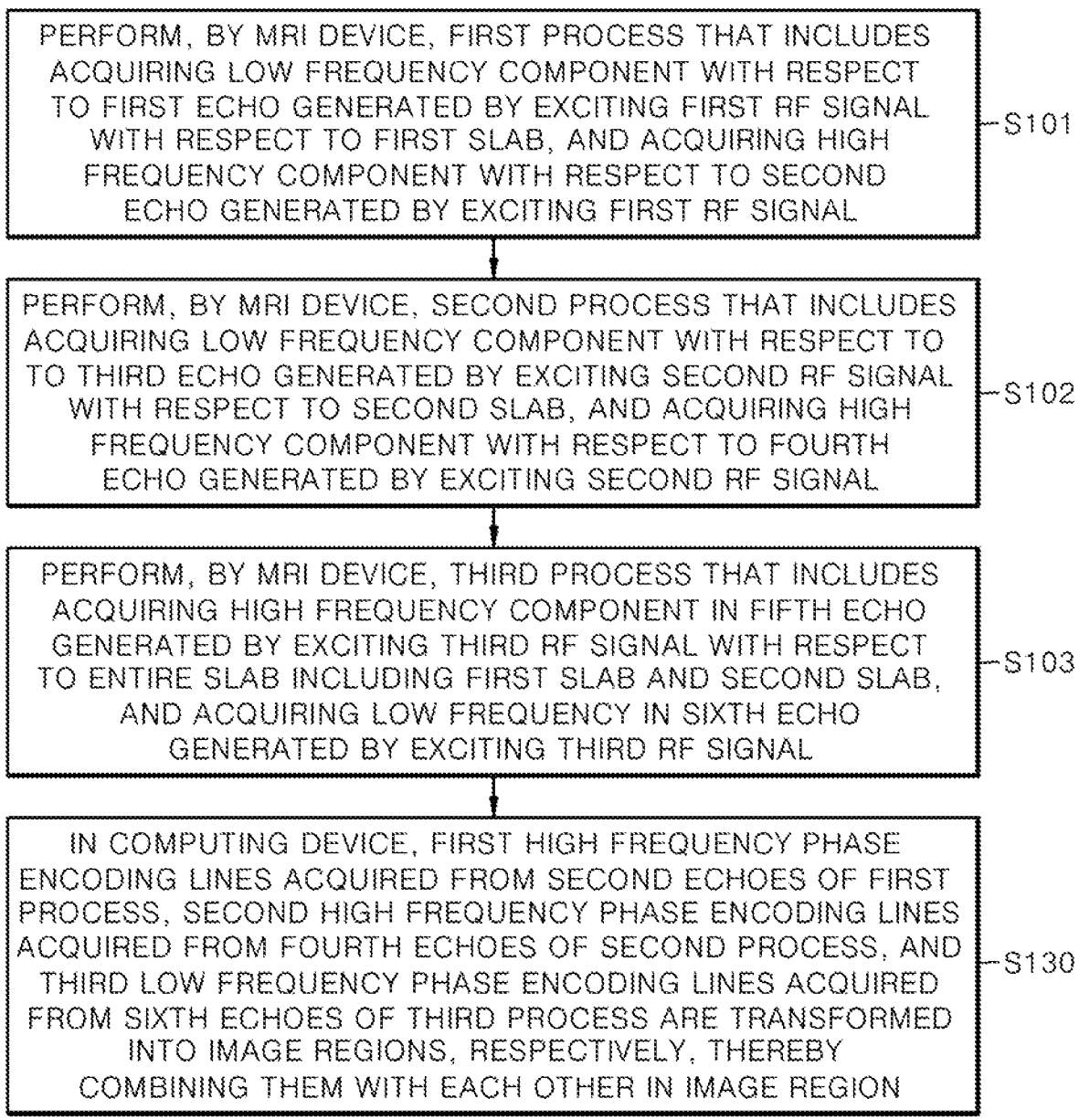
FIG. 15 is a flowchart illustrating a data acquisition method according to a fourteenth embodiment of the present invention.

FIG. 15 is a flowchart illustrating a data acquisition method according to a fourteenth embodiment of the present invention.

In operation S101, the MRI device may perform a first process that includes acquiring a low frequency component with respect to the first echo generated by exciting the first RF signal with respect to the first slab, and acquiring a high frequency component with respect to the second echo generated by exciting the first RF signal.

In operation S102, the MRI device may perform a second process that includes acquiring a low frequency component with respect to the third echo generated by exciting the second RF signal with respect to the second slab, and acquiring a high frequency component with respect to the fourth echo generated by exciting the second RF signal.

In operation S103, the MRI device may perform a third process that includes acquiring a high frequency component in a fifth echo generated by exciting a third RF signal with respect to the entire slab including the first slab and the second slab, and acquiring a low frequency in a sixth echo generated by exciting the third RF signal.

In operation S130, in the computing device, first high frequency phase encoding lines acquired from the second echoes of the first process, second high frequency phase encoding lines acquired from the fourth echoes of the second process, and the third low frequency phase encoding lines acquired from the sixth echoes of the third process are transformed into image regions, respectively, thereby combining them with each other in the image region.

Fifteenth Embodiment

Figure 16:
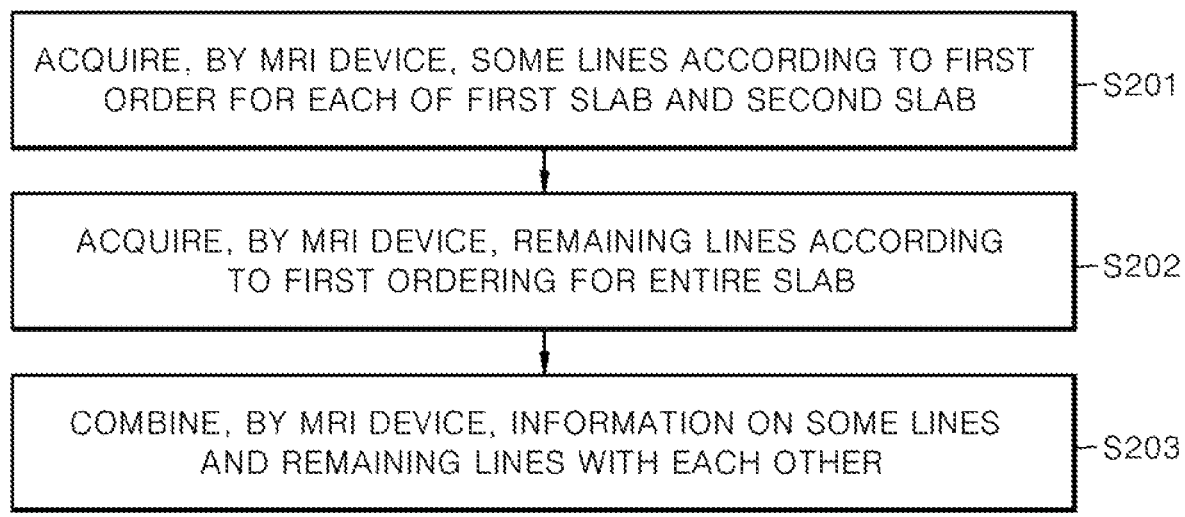
FIG. 16 is a flowchart illustrating a data acquisition method according to a fifteenth embodiment of the present invention.

FIG. 16 is a flowchart illustrating a data acquisition method according to a fifteenth embodiment of the present invention.

In operation S201, the MRI device may acquire some lines according to the first order for each of the first slab and the second slab.

In operation S202, the MRI device may acquire remaining lines according to the first ordering for the entire slab.

In operation S203, the MRI device may combine information on the some lines and the remaining lines with each other.

Sixteenth Embodiment

In a sixteenth embodiment, a semi-permanent recording medium readable by a computing device, in which command codes for operating an MRI device are recorded, may be provided.

The command code allows the MRI device to perform a first process including acquiring a low frequency component with respect to a first echo generated by exciting the first RF signal with respect to a first slab, allows the MRI device to perform a second process including acquiring a low frequency component with respect to a third echo generated by exciting a second RF signal with respect to a second slab, and allows the MRI device to perform in a third process including acquiring a high frequency component in a fifth echo generated by exciting a third RF signal with respect to the entire slab including the first slab and the second slab.

In one embodiment presented herein, processes for acquiring two echoes after exciting the RF signal are presented. At this time, even when using the first echo and the second echo acquired in each process, the object of the present invention can be achieved but only the first echo acquired in each process can achieve the object of the present invention. Some claims of this patent application disclose inventions consisting solely of the first echoes, and other claims also disclose inventions constructed using the second echoes together with the first echoes.

Figure 17:
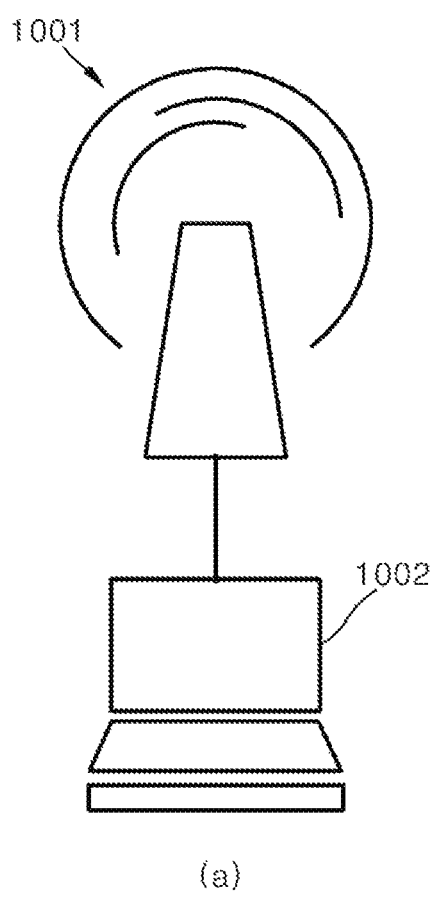
FIG. 17 shows a connection relationship between an MRI device and a computing device according to an embodiment of the present invention.
Figure 17:
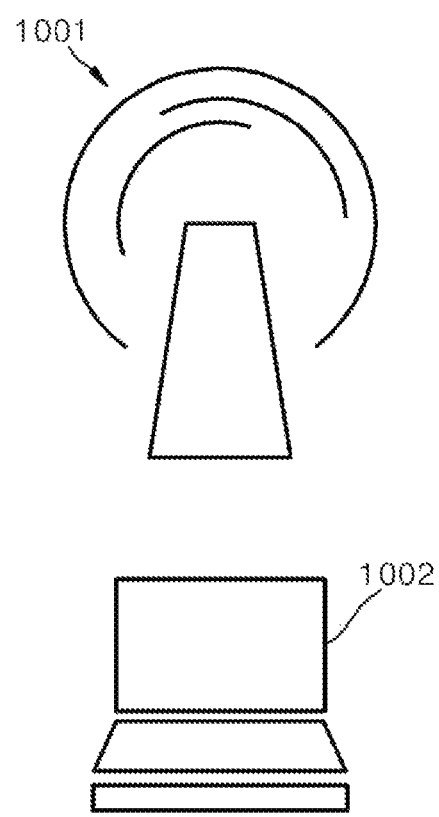

FIG. 17 shows a connection relationship between an MRI device and a computing device according to an embodiment of the present invention.

That is, the MRI device 1001 and the computing device 1002 of FIG. 17 represent the MRI device and the computing device mentioned with reference to FIGS. 12 to 16, respectively.

In FIG. 17(a), the MRI device 1001 and the computing device 1002 may be connected to each other by a wired cable or wirelessly to operate in mutual agreement.

FIG. 17(b) illustrates a state in which the MRI device 1001 and the computing device 1002 are separated from each other. In this case, the data acquired from the MRI device 1001 may be copied to the computing device 1002 using, for example, a mobile device (e.g., USB).

It will be apparent to those skilled in the art that various modifications and variations may be made in the present invention without departing from the spirit or essential characteristics thereof. The contents of each claim may be combined with other claims without departing from the scope of the claims.

The invention claimed is:

1. A data acquisition method using one or more echoes, the method comprising:
performing, by an MRI device, a first process that includes acquiring a low frequency component of a first echo generated by exciting a first RF signal with respect to a first slab;
performing, by the MRI device, a second process that includes acquiring a low frequency component of a third echo generated by exciting a second RF signal with respect to a second slab;
performing, by the MRI device, a third process that includes acquiring a high frequency component of a fifth echo generated by exciting a third RF signal with respect to an entire slab including the first slab and the second slab; and
generating, by a computing device, an entire MRI image by combining the low frequency component of the first echo, the low frequency component of the third echo, and the high frequency component of the fifth echo.

2. The method of claim 1, wherein the first process further comprises acquiring a high frequency component with respect to a second echo generated by exciting the first RF signal with respect to the first slab,
the second process further comprises acquiring a high frequency component with respect to a fourth echo generated by exciting the second RF signal with respect to the second slab, and
the third process further comprises acquiring a low frequency component in a sixth echo generated by exciting the third RF signal with respect to the entire slab including the first slab and the second slab.

3. The method of claim 2, wherein the first echo is an echo generated earlier than the second echo, the third echo is an echo generated earlier than the fourth echo, and the fifth echo is an echo generated earlier than the sixth echo.

4. The method of claim 2, wherein the first echo is a first echo generated by exciting the first RF signal, the second echo is a second echo generated by exciting the first RF signal, the third echo is the first echo generated by exciting the second RF signal, the fourth echo is a second echo generated by exciting the second RF signal, the fifth echo is a first echo generated by exciting the third RF signal, and the sixth echo is a second echo generated by exciting the third RF signal.

5. The method of claim 1, wherein
the first process is configured to excite the first RF signal a plurality of times, and
each time the first RF signal is excited, the first echo is configured to acquire low frequency lines among K-space lines in a predetermined order, and
the second process is configured to excite the second RF signal a plurality of times, and
each time the second RF signal is excited, the third echo is configured to acquire low frequency lines among K-space lines in a predetermined order, and
the third process is configured to excite the third RF signal a plurality of times, and
each time the third RF signal is excited, the fifth echo is configured to acquire high frequency lines among K-space lines in a predetermined order.

6. The method of claim 2, wherein
the first process is configured to excite the first RF signal a plurality of times, and
each time the first RF signal is excited, the first echo acquires low frequency lines among K-space lines in a predetermined order, and
in the second echo, high-frequency lines among K-space lines are acquired in a predetermined order,
the second process is configured to excite the second RF signal a plurality of times, and
each time the second RF signal is excited, the third echo acquires low frequency lines among K-space lines in a predetermined order, and
in the fourth echo, high-frequency lines among the K-space lines are acquired in a predetermined order, and
the third process is configured to excite the third RF signal a plurality of times, and
each time the third RF signal is excited, the fifth echo acquires high frequency lines among K-space lines in a predetermined order, and
in the sixth echo, low-frequency lines among K-space lines are acquired in a predetermined order.

7. The method of claim 1, wherein the generating comprises, generating, the computing device, a first low frequency sub-image by transforming first low frequency phase encoding lines acquired in the first echo of the first process into an image region;
generating, by the computing device, a second low frequency sub-image by transforming second low frequency phase encoding lines acquired in the third echo of the second process into an image region;
generating, by the computing device, a third low frequency sub-image by combining the first low frequency sub-image and the second low frequency sub-image;
transforming, by the computing device, the third low frequency sub-image into a frequency domain to acquire a first low frequency data set; and
acquiring, by the computing device, first K-space data by combining the first low frequency data set and the third high frequency phase encoding lines acquired in the fifth echo of the third process in a frequency domain.

8. The method of claim 2, wherein the generating comprises, generating, by the computing device, a first high frequency sub-image by transforming first high frequency phase encoding lines acquired in the second echo of the first process into an image region;
generating, by the computing device, a second high frequency sub-image by transforming second high frequency phase encoding lines acquired in the fourth echo of the second process into an image region;
generating, by the computing device, a third high frequency sub-image by combining the first high frequency sub-image and the second high frequency sub-image;
transforming, by the computing device, the third high frequency sub-image into a frequency domain to acquire a second high frequency data set; and
acquiring, by the computing device, second K-space data by combining the second high frequency data set and the third low frequency phase encoding lines acquired in the sixth echo of the third process with each other in a frequency domain.

9. The method of claim 1, wherein the generating comprises, transforming, by the computing device, first low frequency phase encoding lines acquired in the first echo of the first process into a first image region data, second low frequency phase encoding lines acquired in the third echo of the second process into a second image region data, and third high frequency phase encoding lines acquired in the fifth echo of the third process into a third image region data; and combining the first image region data, the second image region data, and the third image region data with each other in an image region.

10. The method of claim 2, transforming, by the computing device, first high frequency phase encoding lines acquired in the second echo of the first process into a first image region data, second high frequency phase encoding lines acquired in the fourth echo of the second process into a second image region data, and third low frequency phase encoding lines acquired in the sixth echo of the third process into a first image region data; and
combining the first image region data, the second image region data, and the third image region data with each other in an image region.

11. The method of claim 2, wherein shooting conditions in the first echo and shooting conditions in the second echo are different from each other.

12. The method of claim 2, wherein Time of Flight MR angiogram is acquired at a time of the first echo, and Susceptibility weighted imaging is acquired at a time of the second echo.

13. The method of claim 2, further comprising acquiring an arterial image using data acquired from the first echo, the third echo, and the fifth echo, and acquiring a venous image using data acquired from the second echo, the fourth echo, and the sixth echo.

14. The method of claim 2, further comprising:
acquiring some lines according to a first ordering in the first echo with respect to the first slab,
acquiring some lines according to a second ordering in the second echo,
acquiring some lines according to a third ordering in the third echo with respect to the second slab,
acquiring some lines according to a fifth ordering in the fourth echo,
acquiring at least some of the remaining lines according to a fifth ordering in the fifth echo with respect to the entire slab, and
acquiring at least some of the remaining lines according to a sixth ordering in a sixth echo.

15. A data acquisition method using a plurality of echoes, the method comprising:
performing, by an MRI device, a first process that includes acquiring a first frequency component of a first echo generated by exciting a first RF signal with respect to a first slab;
performing, by the MRI device, a second process that includes acquiring a second frequency component of a second echo generated by exciting a second RF signal with respect to a second slab;
performing, by the MRI device, a third process that includes acquiring a third frequency component of a third echo generated by exciting a third RF signal with respect to an entire slab including the first slab and the second slab; and
generating, by a computing device, an entire MRI image by combining the first frequency component, the second frequency component, and the third frequency component,
wherein,
the first frequency component is a low frequency component of the first echo, the second frequency component is a low frequency component of the second echo, and the third frequency component is a high frequency component of the third echo, or
the first frequency component is a high frequency component of the first echo, the second frequency component is a high frequency component of the second echo, and the third frequency component is a low frequency component of the third echo.

16. A computer-readable non-transitory storage medium in which instruction codes for operating an MRI device are recorded,
wherein the instruction codes are configured to allow an MRI device to perform a first process that includes acquiring a low frequency component of a first echo generated by exciting a first RF signal with respect to a first slab,
allow the MRI device to perform a second process that includes acquiring a low frequency component of a third echo generated by exciting a second RF signal with respect to a second slab,
allow the MRI device to perform a third process that includes acquiring a high frequency component of a fifth echo generated by exciting a third RF signal with respect to an entire slab including the first slab and the second slab; and allow the MRI device to generate an entire MRI image by combining the low frequency component of the first echo, the low frequency component of the third echo, and the high frequency component of the fifth echo.

\* \* \* \* \*